US012806084B2

(12) United States Patent
Bäck et al.

(10) Patent No.: US 12,806,084 B2
(45) Date of Patent: Nov. 24, 2026

(54) DISPOSABLE ABSORBENT PANT-TYPE ARTICLE AND A METHOD FOR PRODUCING A DISPOSABLE ABSORBENT PANT-TYPE ARTICLE

(71) Applicant: Essity Hygiene and Health Aktiebolag, Gothenburg (SE)

(72) Inventors: Lucas Bäck, Gothenburg (SE); Fanny Stenholm, Gothenburg (SE); Helena Wallin, Gothenburg (SE); Johannes Lanooij, Ah Zeist (NL)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 99 days.

(21) Appl. No.: 18/864,101

(22) PCT Filed: May 20, 2022

(86) PCT No.: PCT/EP2022/063750
§ 371 (c)(1),
(2) Date: Nov. 8, 2024

(87) PCT Pub. No.: WO2023/222242
PCT Pub. Date: Nov. 23, 2023

(65) Prior Publication Data

US 2025/0325413 A1 Oct. 23, 2025

(51) Int. Cl.
*A61F 13/496* (2006.01)
*A61F 13/49* (2006.01)

(52) U.S. Cl.
CPC ...... *A61F 13/496* (2013.01); *A61F 13/49012* (2013.01); *A61F 2013/49038* (2013.01)

(58) Field of Classification Search
CPC .............. A61F 13/49012; A61F 13/496; A61F 13/49019; A61F 13/49061;
(Continued)

(56) References Cited

U.S. PATENT DOCUMENTS

2013/0211363 A1* 8/2013 LaVon ................ A61F 13/4902 604/385.3
2017/0105885 A1* 4/2017 Shirai ............... A61F 13/15601
(Continued)

FOREIGN PATENT DOCUMENTS

EP 3251642 A1 12/2017
JP H09290003 A 11/1997
(Continued)

OTHER PUBLICATIONS

International Search Report (PCT/ISA/210) and Written Opinion (PCT/ISA/237) mailed on Jan. 4, 2023 by the European Patent Office as the International Searching Authority for International Application No. PCT/EP2022/063750. (12 pages).
(Continued)

*Primary Examiner* — Philip R Wiest
(74) *Attorney, Agent, or Firm* — Buchanan Ingersoll & Rooney PC

(57) ABSTRACT

A disposable pant-type article including front and rear body panels, the body panels being constituted by front body panel material which is elastically stretchable in a transverse direction and with a crotch region. An absorbent core is arranged with front and rear end parts of the absorbent core overlapping with the body panels in front and rear overlap areas. The pant-type article includes at least one body panel zone with reduced elasticity, which is arranged in an overlap area between the absorbent core and one of the front body panel and the rear body panel and which extends in the longitudinal direction outside the overlap area towards the waist opening of the article.

31 Claims, 10 Drawing Sheets

(58) Field of Classification Search
CPC .......... A61F 13/15699; A61F 13/15707; A61F 2013/49022; A61F 2013/49038
See application file for complete search history.

(56) References Cited

U.S. PATENT DOCUMENTS

| | | | | |
|---|---|---|---|---|
| 2018/0014984 | A1* | 1/2018 | Sakai | A61F 13/15 |
| 2018/0256410 | A1* | 9/2018 | Bäck | B29C 65/74 |
| 2021/0228424 | A1* | 7/2021 | Tsunoda | A61F 13/49012 |
| 2022/0071815 | A1* | 3/2022 | Sasayama | A61F 13/15585 |

FOREIGN PATENT DOCUMENTS

| | | | | |
|---|---|---|---|---|
| JP | 2004236850 | A | 8/2004 | |
| JP | 2015071006 | A | 4/2015 | |
| JP | 2015171400 | A | 10/2015 | |
| JP | 2017018443 | A | 1/2017 | |
| JP | 2017018444 | A | 1/2017 | |
| JP | 2018526149 | A | 9/2018 | |
| JP | 2019208814 | A | 12/2019 | |
| JP | 2020188871 | A | 11/2020 | |
| JP | 2020192123 | A | 12/2020 | |
| JP | 2021118829 | A | 8/2021 | |
| WO | WO-2014208781 | A2 * | 12/2014 | A61F 13/49061 |
| WO | 2015108091 | A1 | 7/2015 | |
| WO | 2017044013 | A1 | 3/2017 | |
| WO | 2017044014 | A1 | 3/2017 | |

OTHER PUBLICATIONS

Office Action (Notice of Reasons for Rejection) issued on Mar. 24, 2026, by the Japanese Patent Office in corresponding Japanese Patent Application No. 2024-568844, and an English Translation of the Office Action. (30 pages).

* cited by examiner

DISPOSABLE ABSORBENT PANT-TYPE ARTICLE AND A METHOD FOR PRODUCING A DISPOSABLE ABSORBENT PANT-TYPE ARTICLE

TECHNICAL FIELD

The present disclosure pertains to an elastic disposable absorbent pant-type article comprising:

a front body panel constituted by a front body panel material which is elastically stretchable in a transverse direction of the pant-type article, a rear body panel constituted by a rear body panel material which is elastically stretchable in the transverse direction of the pant-type article and a crotch region located between the front body panel and the rear body panel. An absorbent core is arranged with a central part of the absorbent core in the crotch region and with a front end part of the absorbent core overlapping with the front body panel in a front overlap area and with a rear end part of the absorbent core overlapping with the rear body panel in a rear overlap area. A first front panel side edge is joined to a first rear panel side edge in a first side seam and a second front panel side edge is joined to a second rear panel side edge in a second side seam thereby forming a waist opening and two leg openings in the disposable pant-type article.

The disclosure further pertains to a continuous method of producing elastic disposable pant-type articles using at least one continuous elastic web material.

BACKGROUND

In the art of disposable pant-type articles and in particular disposable pant-type articles which are intended for use by adult users, the articles should meet high demands on fit, comfort and have a tailored and underwear like appearance while at the same time meeting equally high demands on absorbency and leakage protection. Disposable absorbent articles are articles which are intended to be discarded after a single use and not be laundered or otherwise restored for repeated use.

Pant-type articles of this kind are relatively complex products involving multiple components which are combined in high-speed processes to form the absorbent article. Such components include nonwoven components, barrier components, elastic components and usually an absorbent core which may be provided in the form of an absorbent assembly including a barrier layer and a liquid permeable topsheet which together enclose the absorbent core.

Elastic web materials, such as elastic nonwoven materials, and elastic polymeric films are used to create pant-type articles with body-conforming properties resembling those of high-quality textile underwear. In addition, it is common to enhance fit and leakage security by arranging pre-tensioned elastic elements along all or selected parts of the waist opening and leg openings of the pant-type article.

In disposable pant-type articles comprising an absorbent core, the fit and body conforming properties conveyed by elastic materials in the articles may be negatively affected by an absorbent core, as the absorbent materials used in disposable articles are non-elastic and tend to increase the stiffness of the article within an area of the article in which the absorbent core is arranged. The stiffened portions of the pant-type article detract from the fit and body conformance of the article and may even cause the article to bulge away from the body of a user. On the other hand, the elastic materials may negatively affect the properties of an absorbent core, as the core may become wrinkled or otherwise deformed in a non-desired manner under the influence of contractive forces exerted by elastic materials in the article.

Accordingly, there exists an ongoing need for improved elastification of a disposable absorbent pant-type article.

SUMMARY

Disposable pant-type articles having good functionality, fit and comfort, may be provided at least in part by the features of claim 1 and may be produced according to claim 26. Variations of the disclosure are set out in the dependent claims.

Disclosed herein is a disposable pant-type article, the article having a longitudinal direction and a transverse direction, the article comprising:

a front body panel being constituted by an elastic front body panel material, the front body panel material being elastically stretchable in the transverse direction;

a rear body panel being constituted by an elastic rear body panel material, the rear body panel material being elastically stretchable in the transverse direction;

a crotch region being located between the front body panel and the rear body panel;

an absorbent core being arranged with a central part of the absorbent core being located in the crotch region and with a front end part of the absorbent core overlapping with the front body panel in a front overlap area and with a rear end part of the absorbent core overlapping with the rear body panel in a rear overlap area;

a first front panel side edge being joined to a first rear panel side edge in a first side seam;

a second front panel side edge being joined to a second rear panel side edge in a second side seam;

a waist opening, defined by a front panel waist edge and a rear panel waist edge;

a first leg edge defining a first leg opening; and a second leg edge defining a second leg opening;

the disposable pant-type article further comprising at least one a body panel zone with reduced elasticity, the at least one body panel zone with reduced elasticity being arranged in the overlap area between the absorbent core and one of the front body panel and the rear body panel, the at least one body panel zone with reduced elasticity extending in the longitudinal direction outside the overlap area towards the waist opening and having a tapering shape in the longitudinal direction of the disposable pant-type article, with an extension of the at least one body panel zone with reduced elasticity in the transverse direction adjacent the waist opening being smaller than an extension of the at least one body panel zone with reduced elasticity in the transverse direction adjacent the absorbent core.

The at least one body panel zone with reduced elasticity as disclosed herein is a zone in a body panel which has been treated to render the body panel material in the treated body panel zone less elastic than a non-treated part of the body panel material. A zone with reduced elasticity is also referred to herein as a "heat-treated zone", or a "treated zone".

The at least one body panel zone with reduced elasticity as disclosed herein may be a front body panel zone with reduced elasticity.

The disposable pant-type article may further comprise a rear body panel zone with reduced elasticity, the rear body panel zone with reduced elasticity being arranged in the overlap area between the absorbent core and the rear body panel. The rear body panel zone with reduced elasticity may have a tapering shape in the longitudinal direction of the disposable pant-type article, with an extension of the rear one body panel zone with reduced elasticity in the transverse direction adjacent the waist opening being smaller than an extension of the rear body panel zone with reduced elasticity in the transverse direction adjacent the absorbent core.

The at least one body panel zone with reduced elasticity may have any tapering shape such as a triangular shape, a trapezoidal shape, a drop-shape, or a funnel shape. Furthermore, the body panel zone with reduced elasticity may have a mushroom shape or a club-shape. The contour of the body panel zone with reduced elasticity is preferably continuous, without stepwise or sharp changes to promote a smooth transition between the body panel zone with reduced elasticity and the body panel material outside the body panel zone with reduced elasticity.

The at least one body panel zone with reduced elasticity as disclosed herein may have a continuously tapering shape in a part of the body panel zone with reduced elasticity which is arranged between an end edge of the absorbent core and the waist edge of the body panel in which the body panel zone with reduced elasticity is arranged. Alternatively, the at least one body panel zone with reduced elasticity may have a continuously tapering shape in a part of the body panel zone with reduced elasticity which is arranged between an end edge of an absorbent assembly, if present, and the waist edge of the body panel in which the body panel zone with reduced elasticity is arranged.

By forming zones with reduced elasticity having a narrower part at the waist portion of the article and a broader part at the absorbent core of the article, the article will have stronger elasticity, i.e., a greater retractive force, at the waist portion. Furthermore, the increasing elasticity in the front body panel and/or in the rear body panel of the pant-type absorbent article will cause the side seams to assume an inwardly sloping configuration when the pant-type article is in a non-tensioned state. Such shaped side seams conform better to the shape of the hips of a user.

The at least one body panel zone with reduced elasticity may terminate at an elastic waistband which is arranged at the waist opening and which provides the article with waist elastic, or the body panel zone with reduced elasticity may continue beneath an elastic waistband which has been applied such that it overlaps with the front and rear body panels. When producing a pant-type article as disclosed herein, an elastic waistband is preferably applied after treating the material of the front body panel and/or the rear body panel to form the at least one body panel zone with reduced elasticity. The waistband may be applied such that it fully or partly overlaps the body panel zone with reduced elasticity at the waist opening and provides the article with a fully functional, waist-encircling elastic waistband.

A part of the front body panel zone with reduced elasticity which extends outside the front overlap zone may have a tapering shape with a tapering angle a being defined between a line of inclination of a portion of the front body panel zone with reduced elasticity which is located between a forward end of an absorbent assembly and a front waist edge of the front body panel, and a line, which is parallel to the longitudinal direction of the pant-type absorbent article. The line of inclination is drawn from a point where the front body panel zone with reduced elasticity intersects with a line which is parallel to the transverse direction of the pant-type absorbent article, and which is drawn through a forward end point of an absorbent assembly; to a point where the front body panel zone with reduced elasticity intersects with the front waist edge of the front body panel.

In a disposable pant-type article as disclosed herein, comprising an absorbent core which is not part of an absorbent assembly, the line of inclination is drawn from a point where the front body panel zone with reduced elasticity intersects with a line which is parallel to the transverse direction of the pant-type absorbent article and which is drawn through a forward end point of the absorbent core; to a point where the front body panel zone with reduced elasticity intersects with the front waist edge of the front body panel.

The tapering angle $\alpha$ of the front body panel zone with reduced elasticity may be in the range of from 3° to 35°, preferably from 7° to 25°.

A part of the rear body panel zone with reduced elasticity which extends outside the rear overlap zone may have a tapering shape with a tapering angle a being defined between a line of inclination of a portion of the rear body panel zone with reduced elasticity which is located between a rearward end of an absorbent assembly and a rear waist edge of the rear body panel, and a line, which is parallel to the longitudinal direction of the pant-type absorbent article. The line of inclination is drawn from a point where the rear body panel zone with reduced elasticity intersects with a line which is parallel to the transverse direction of the pant-type absorbent article, and which is drawn through a rearward end point of an absorbent assembly; to a point where the rear body panel zone with reduced elasticity intersects with the rear waist edge of the rear body panel.

In a disposable pant-type article as disclosed herein, comprising an absorbent core which is not part of an absorbent assembly, the line of inclination is drawn from a point where the rear body panel zone with reduced elasticity intersects with a line which is parallel to the transverse direction of the pant-type absorbent article, and which is drawn through a rearward end point of the absorbent core; to a point where the rear body panel zone with reduced elasticity intersects with the rear waist edge of the rear body panel.

The tapering angle $\alpha$ of the rear body panel zone with reduced elasticity may be in the range of from 3° to 35°, preferably from 7° to 25°.

The elastically stretchable front body panel and/or the elastically stretchable rear body panel may comprise or consist of an elastic laminate, the elastic laminate comprising at least a first layer of nonwoven material and an elastic layer. The term "elastic layer" as used herein, refers to a layer of a coherent inherently elastic web material, such as an elastic nonwoven material or an elastic film.

Although the first layer of nonwoven material may be an elastic nonwoven material, it may generally be preferred that the first layer of nonwoven material is a non-elastic layer.

The elastic laminate may comprise a second layer of nonwoven material and the elastic layer is an intermediate elastic layer arranged between the first and second layers of nonwoven material. The laminate may comprise a further layer or further layers in addition to the first and second layers of nonwoven material and the elastic layer. The elastic laminate may be a three layer laminate, with outer non-elastic nonwoven layers and an intermediate elastic film or nonwoven layer sandwiched therebetween.

As for the first layer of nonwoven material, it may be preferred that the second layer of nonwoven material is a non-elastic layer.

The elastic layer in the elastic laminates disclosed herein may comprise or consist of a layer of elastic film or may comprise or consist of a layer of elastic nonwoven material.

Laminates comprising both an elastic film layer and an elastic nonwoven layer may also be used in the disposable pant-type articles as disclosed herein.

At least two layers of the elastic laminates for use in the pant-type articles as disclosed herein may be bonded together with a plurality of discrete bonds. The bonds are preferably arranged in a regular bonding pattern which is visible on an external surface of the elastic body panel including being visible on the external surface of the elastic body panel in the body panel zone with reduced elasticity. The external surface of the body panel is a surface of the body panel which forms part of the outside surface of the pant-type article and is a surface of the body panel which will be facing away from the body of a wearer of the pant-type article. The outside surface of the pant-type article may also be referred to as the garment-facing surface of the pant-type article. Accordingly, the bond pattern on the body panel is visible from the outside of the pant-type article.

In a three-layer laminate, such as in a laminate of first and second outer nonwoven webs and an intermediate elastic layer, such as an elastic film layer or an elastic nonwoven layer, all three layers may be bonded together in a same bonding step. In such instance, the bonding pattern will be visible both on the external, garment-facing surface of a body panel produced from the three-layer laminate as well as on the opposing inner, body-facing surface of the body panel.

The bonding pattern may be a pattern of discrete bonding elements, such as a pattern of uniformly distributed discrete bonding elements. Each discrete bonding element may have a surface area in the order of 0.1 $mm^2$ to 3.0 $mm^2$. It may be preferred that the surface area of the individual bond areas is in the lower part of the range, such as from 0.1 $mm^2$ to 1.5 $mm^2$ or from 0.1 $mm^2$ to 1.0 $mm^2$.

The total bond area may be in the range of from 4% to 13%, preferably in the range of from 5% to 10%.

The bonding elements may have any useful shape or combination of shapes including rounded shapes such as circular and oval shapes, polygonal shapes such as triangular, square/rectangular and rhombic shapes, as well as rod-shaped bonding elements, figurative bonding elements, etc.

The bonding pattern may be formed by ultrasonic bonding or heat bonding (also referred to herein as thermo-bonding), the bonding elements being formed by locally heating the layers which are bonded together to cause thermoplastic material in the laminated layers to soften and/or melt and subsequently consolidate in the bonds.

The elastically stretchable front body panel and the elastically stretchable rear body panel of the pant-type articles as disclosed herein may comprise or consist of a stretch-bonded laminated elastic web material. A stretch-bonded laminate is formed by bonding the layers of the laminate together while holding the layer of elastic material in a stretched state, at least in a machine direction and optionally also in a cross machine direction of the layer of elastic material. In the pant-type articles as disclosed herein, the elastic laminates are arranged in the articles with the machine direction corresponding to the transverse direction of the pant-type article and with the cross machine direction corresponding to the longitudinal direction of the pant-type article.

The layers of the bonded laminate may be coextensive, i.e., they may be completely overlapping with each other. Alternatively, the elastic material layer may have a smaller extension in the cross machine direction of the laminate than the nonwoven layer or layers, i.e., the elastic material layer may have a smaller extension in the longitudinal direction of the pant-type article.

The bonding elements are distributed over the body panel in the regular bonding pattern over the full area of the body panel, i.e., also in the zone with reduced elasticity. In other words, the bonding pattern is the same in the body panel zone with reduced elasticity as in the other parts of the body panel. Moreover, the surface structure of the elastic laminate has not been modified or has not been significantly modified by the heat treatment to which the elastic laminate has been subjected when creating the zone with reduced elasticity. Thereby, the visual appearance of the body panel material is the same, or substantially the same over the full surface of the body panel. This has the effect of masking or concealing the presence of the absorbent core which is located inside the body panel in the body panel zone with reduced elasticity, thereby enhancing the likeness of the disposable pant-type article to ordinary underwear.

Nonwoven material layers or webs in the elastic laminates as disclosed herein may be spunbond, air laid, wet laid, carded, electro spun or meltblown nonwovens. Composite webs such as spunbond-meltblown-spunbond (SMS) and similar materials may also be used. The nonwoven material may be bonded by any suitable technique, such as by needling, hydroentangling, ultrasonic welding, or thermo-bonding.

The fibres of the nonwoven materials used herein may be man-made fibres or mixtures of man-made and natural fibres. Man-made fibres include mono-component, bi-component and multicomponent fibres of polymers such as polyolefins, polyesters, polyacrylates, etc., as well as regenerated fibres such as viscose fibres and modal fibres. Natural fibres are for instance cellulosic fibres such as pulp fibres, cotton fibres, flax, hemp, etc.

In a laminate in which the layers are bonded by ultrasonic bonding or heat bonding, the nonwoven materials which are used to form the laminate should contain a sufficient amount of thermoplastic material to allow the bonding elements to be formed. Examples of suitable thermoplastic polymers for use in the fibres of the nonwoven webs as disclosed herein are polyethylene polypropylene and other polyolefin homopolymers and copolymers and polyesters. The fibres may be mono-component fibres, bi-component fibres or multi-component fibres. The heat-bondable nonwoven webs preferably contain at least 50% thermoplastic fibres and more preferably at least 80% thermoplastic material.

As an alternative to being constituted by an elastic laminate, at least a portion of the elastically stretchable front body panel and/or the elastically stretchable rear body panel may consist of a single-layer elastic nonwoven material.

The elasticity of the body panel material in the front body panel zone with reduced elasticity and/or the elasticity of the body panel material in the rear body panel zone with reduced elasticity may be from 0% to 70% of the elasticity of the body panel material outside the body panel zone with reduced elasticity, such as from 30% to 70% of the elasticity of the body panel material outside the body panel zone with reduced elasticity, such as from 40% to 70% of the elasticity of the body panel material outside the body panel zone with reduced elasticity and preferably from 30% to 60% of the elasticity of the body panel material outside the body panel zone with reduced elasticity.

The body panel material may have been heat-treated to eliminate the elasticity in a body panel zone with reduced elasticity. Alternatively, the material in the body panel zone with reduced elasticity may retain some elasticity, however at a lower level than non-treated parts of the elastic body panel material.

The elastically stretchable front body panel may be formed from a continuous front body panel web which extends transversely across the width of the pant-type article between the first and the second front panel side edges and/or the elastically stretchable rear body panel may be formed from a continuous rear body panel web which extends transversely across the width of the pant-type article between the first and the second rear panel side edges.

The crotch region of the disposable pant-type article as disclosed herein may comprise a non-elastic crotch web material, such as a non-elastic nonwoven web. A less-elastic or nonelastic crotch region may alternatively be created by treating, such as by heat-treating, a portion of an elastic web material to create a crotch zone with reduced elasticity in the elastic web material in the crotch region.

The pant-type articles as disclosed herein may be of the kind having a two-part chassis with a crotch panel which is connected to the front body panel along a front body panel crotch edge, and which is connected to the rear body panel along a rear body panel crotch edge. Alternatively, the pant-type article may have a unitary chassis comprising a non-elastic outer or inner cover web extending the full distance between the front body panel waist edge and the rear body panel waist edge, the cover web constituting a non-elastic layer of each of the front body panel and the rear body panel and constituting the crotch web material in the crotch region of the pant-type article.

In the pant-type disposable articles as disclosed herein, the absorbent core may form part of an absorbent assembly, the absorbent assembly comprising the absorbent core, a liquid permeable topsheet and a liquid impermeable backsheet, the absorbent core being sandwiched between the liquid permeable topsheet and the liquid impermeable backsheet.

The disposable pant-type articles as disclosed herein may comprise an elastic waist feature. The elastic waist feature may form a continuous waistband encircling the waist opening of the disposable pant-type article, or may be applied only to selected portions of the waist opening, such as only along central portions of the waist edge of the front and rear body panels or only along the waist edge of the rear body panel, etc.

The elastic waist feature may be completely overlapping with the front body panel and/or with the rear body panel and may share a waist edge with the corresponding front body panel and/or rear body panel.

The elastic waist feature may be completely overlapping with the front body panel and/or with the rear body panel or may be applied to a waist edge of the front body panel and/or rear body panel and protrude beyond the waist edge of the corresponding front body panel and/or rear body panel.

The elastic waist feature may comprise one or more elastic elements. The waist feature may comprise a plurality of elastic strands or elastic bands. Alternatively, the elastic waist feature may comprise or consist of a band of elastic material, such as elastic nonwoven, elastic foam or elastic film. The elastic waist feature may be attached to the front body panel and/or to the rear body panel as a prefabricated component, such as a waistband component comprising two layers of carrier web with multiple elastic strands or bands attached between the layers of carrier web. An elastic waist feature comprising multiple elastic elements such as strands or bands may alternatively be formed directly on the elastic body panel material by applying the elastic elements to the body panel along a waist edge of the body panel and subsequently covering the elastic elements by a cover web, such as a nonwoven cover web.

The elastic waist feature provides the article with waist elastic which is in addition to the elastic provided by the elastic material in the front body panel and the rear body panel. The elastic waist feature may be a component of the disposable pant-type article which produced separately from the body panel material of the front body panel and the rear body panel or may be incorporated in the front body panel material and/or in the rear body panel material by being applied between layers of the front body material and/or the rear body panel material. The elastic waist feature is preferably applied after the body panel zone or body panel zones with reduced elasticity has/have been formed in the body panel material, to avoid reducing the elasticity in the elastic waist feature.

Disclosed herein is also a method of producing a disposable pant-type article, such as the disposable pant-type article disclosed herein, the method comprising:

- continuously feeding a tensioned elastic web material in a machine direction, the elastic web material having a first side edge and a second side edge;
- creating zones with reduced elasticity in the elastic web material by exposing portions of the elastic web material to heat treatment, the zones with reduced elasticity being spaced-apart in the machine direction;
- forming at least a first body panel web as a part of a composite web of interconnected precursor articles from the elastic web material, the composite web of precursor articles having a first waist edge and a second waist edge, the tensioned first body panel web comprising at least a portion of each of the spaced-apart zones with reduced elasticity each portion of each of the spaced-apart zones with reduced elasticity forming a body panel zone with reduced elasticity in the first body panel web, each body panel zone with reduced elasticity having a tapering shape in the cross machine direction of the tensioned first body panel web;
- arranging the tensioned first body panel web side-by-side with a tensioned elastic second body panel web in the composite web of interconnected precursor articles and with a distance between the tensioned first body panel web and the tensioned second body panel web in a cross machine direction and with the body panel zones with reduced elasticity in the first body panel web arranged with each body panel zone with reduced elasticity tapering towards the first waist edge of the composite web of precursor articles;
- intermittently applying absorbent assemblies to the tensioned first body panel web and the tensioned second body panel web, the absorbent assemblies being applied spaced-apart in the machine direction and being attached with a first end part of each absorbent assembly overlapping a zone of reduced elasticity in the tensioned first body panel web and a second end part of the absorbent assembly overlapping a portion of the tensioned second body panel web;
- folding the composite web of precursor articles along a fold-line extending in the machine direction and bringing the first waist edge of the composite web of precursor articles into alignment with the second waist edge of the composite web of precursor articles;
- forming first and second side seams in each precursor article, the side seams joining the tensioned first body panel web with the tensioned second body panel web and being formed in the cross machine direction along dividing lines between the precursor articles; and severing individual pant-type articles from the composite web of precursor articles.

In the heat treatment step, the heat which is supplied to the elastic web material is preferably controlled to avoid raising the temperature of thermoplastic material in the elastic web material above the melting point of the thermoplastic material. Thereby, the fibrous structure of a nonwoven web comprising or consisting of thermoplastic fibres and forming part of the elastic web material may be retained or at least substantially retained in the elastic web material. The heat supply may be controlled by controlling the heat exposure time and/or the temperature of a heat supply means such as a heating roller.

In the heat treatment step, the elasticity of the elastic web material may be reduced or completely obliterated. It may be advantageous to retain some degree of elasticity in the area with reduced elasticity, as the difference in appearance of the pant-type article between the non-treated zone and the treated zone may be less noticeable than if the heat-treated zone is completely inelastic. Furthermore, the heat-treatment does not affect or does not substantially affect the surface structure, such as a fibrous structure and a bonding pattern, of an outer surface of the heat-treated elastic body panel material. Thereby, the material in the heat-treated zone is preferably not distinguishable or is at least not readily distinguishable from the non-treated material with the naked eye, which makes the presence of the heat-treated zone less noticeable. An outer cover of an absorbent article having a different appearance where the cover overlaps with an absorbent core may signal the presence of the absorbent core. A uniform appearance of the outer core is therefore highly beneficial in that it may mask the contours of the absorbent core and make the presence of the absorbent core less apparent. A particular benefit of using a bonding pattern of multiple discrete bonding elements when bonding together layers of an elastic laminate web material as disclosed herein, is that the bonding pattern contributes to the masking effect by obscuring the transition between the untreated material and the treated zones with reduced elasticity.

The articles as disclosed herein are thereby more underwear like than prior articles having a completely non-elastic zone within the area of the absorbent core. In addition, by means of the heat treatment of the elastic material in the area of overlap with the absorbent core, the elastic effect from the elastic material on the core is reduced, such that unwanted contraction and deformation of the core may be avoided. At the same time, the remaining elasticity in the heat treated less elastic zone acts to hold the absorbent core in contact with the body of a wearer of the pant-type absorbent article, thereby contributing to reducing bulkiness of the article and to enhance underwear-likeness. By forming zones with reduced elasticity having a narrower part at the waist portion of the article and a broader part at the crotch portion of the article, the article is provided with stronger elasticity at the waist portion. As set out herein, the higher elasticity (SIS) in the front panel and/or in the rear panel of the pant-type absorbent article causes the side seams to assume an inwardly sloping configuration which closely conforms to a user's body over the hips. The absorbent articles as disclosed herein are found to be especially well suited for female users, as they are adapted to the female anatomy.

The elastic web material may be an elastic laminate web material. The elastic laminate web material may be formed by bonding at least a first layer of nonwoven material to an elastic layer, bonding being performed with a plurality of discrete bonds, the bonds being arranged in a bonding pattern.

The method as disclosed herein may further comprise the steps of:

feeding a continuous non-elastic crotch web in the machine direction;

attaching the non-elastic crotch web to the tensioned first body panel web and to the tensioned second body panel web, thereby bridging the distance between the tensioned first body panel web and the tensioned second body panel web, the non-elastic continuous crotch web being attached to the tensioned first body panel web and to the tensioned second body panel web after arranging the tensioned first body panel web side-by-side with the tensioned elastic second body panel web and before applying the absorbent assemblies to the tensioned first body panel web and to the tensioned second body panel web; and forming leg cuts in the composite web of interconnected precursor articles, each leg cut having a closed loop configuration and forming a first leg edge of a leading precursor article and a second leg edge of a trailing precursor article.

The method of producing a disposable pant-type article, such as the disposable pant-type article disclosed herein, may comprise:

continuously feeding a tensioned elastic web material in a machine direction, the elastic web material having a first side edge and a second side edge;

creating zones with reduced elasticity in the elastic web material by exposing portions of the elastic web material to heat treatment, the zones with reduced elasticity being spaced-apart in the machine direction;

forming at least a first body panel web as a part of a composite web of interconnected precursor articles from the elastic web material, the composite web of precursor articles having a first waist edge and a second waist edge, the tensioned first body panel web comprising at least a portion of each of the spaced-apart zones with reduced elasticity each portion of each of the spaced-apart zones with reduced elasticity forming a body panel zone with reduced elasticity in the first body panel web, each body panel zone with reduced elasticity having a tapering shape in the cross machine direction of the tensioned first body panel web;

arranging the tensioned first body panel web side-by-side with a tensioned elastic second body panel web in the composite web of interconnected precursor articles and with a distance between the tensioned first body panel web and the tensioned second body panel web in a cross machine direction and with the body panel zones with reduced elasticity in the first body panel web arranged with each body panel zone with reduced elasticity tapering towards the first waist edge of the composite web of precursor articles;

feeding a non-elastic continuous crotch web in the machine direction;

attaching the crotch web to the tensioned first body panel web and to the tensioned second body panel web, thereby bridging the distance between the front panel crotch edge and the rear panel crotch edge, the non-elastic continuous crotch web being attached to the tensioned first body panel web and to the tensioned second body panel web after arranging the tensioned first body panel web side-by-side with the tensioned elastic second body panel web and before applying the absorbent assemblies to the tensioned first body panel web and the tensioned second body panel web;

intermittently applying absorbent assemblies to the tensioned first body panel web, the crotch web and the tensioned second body panel web, the absorbent assemblies being applied spaced-apart in the machine direction and being attached with a first end part of each absorbent assembly overlapping a zone of reduced elasticity in the tensioned first body panel web and a second end part of the absorbent assembly overlapping a portion of the tensioned second body panel web, the portion of the tensioned second body panel web optionally being a zone of reduced elasticity in the tensioned second body panel web;

forming leg cuts in the composite web of interconnected precursor articles, each leg cut having a closed loop configuration and forming a first leg edge of a leading precursor article and a second leg edge of a trailing precursor article;

folding the composite web of precursor articles along a fold-line extending in the machine direction and bringing the first waist edge of the composite web of precursor articles into alignment with the second waist edge of the composite web of precursor articles;

forming first and second side seams in each precursor article, the side seams joining the tensioned first body panel web with the tensioned second body panel web and being formed in the cross machine direction along dividing lines between the precursor articles; and severing individual pant-type articles from the composite web of precursor articles.

The method for producing absorbent pant-type articles as disclosed herein and involving the application of a crotch web between the tensioned first body panel web and the tensioned second body panel web may further comprise:

providing a pair of crotch elastic members, the pair of crotch elastic members consisting of a first crotch elastic member and a second crotch elastic member;

stretching each crotch elastic member in a longitudinal direction of the crotch elastic member and aligning the longitudinal direction of the crotch elastic member with the cross machine direction; and attaching each stretched crotch elastic member to the crotch web while keeping the crotch elastic member stretched and aligned with the cross machine direction, the first crotch elastic member being spaced apart from the second crotch elastic member with a crotch spacing in the machine direction, a pair of crotch elastic members of a leading precursor article being spaced apart from a pair of crotch elastic members of a trailing precursor article with an article spacing in the machine direction, the article spacing being dependent on a pitch-length of the precursor articles in the composite web of interconnected precursor articles.

As used herein, the pitch-length is the length of each precursor article in the machine direction during production of the pant-type articles as disclosed herein, corresponding to the width direction of a final pant-type article. The pitch-length may be kept the same during the whole production process, up until individual pant-type articles are severed from the composite web of interconnected precursor articles.

The method as disclosed herein may further comprise a step of:

dividing the heat-treated elastic web material in two parts by forming a cut in the elastic web material along a dividing line extending in the machine direction, thereby forming the tensioned first body panel web and the tensioned second body panel web, the tensioned first body panel web having a first side edge being constituted by the first side edge of the elastic web material and having a second side edge being formed by the cut in the elastic web material, the tensioned second body panel web having a first side edge being constituted by the second side edge of the elastic web material and a second side edge being formed by the cut in the elastic web material.

In a method as disclosed herein comprising a step of dividing the heat-treated elastic web material in two parts, the step of arranging the tensioned first body panel web and the tensioned second body panel web side-by-side at a distance from each other in the cross machine direction may involve shifting position of the tensioned first body panel web and the tensioned second body panel web in the cross machine direction, whereby the second side edge of the tensioned first body panel web forms the first waist edge of the composite web of precursor articles and the second side edge of the tensioned second body panel web forms the second waist edge of the composite web of precursor articles. Waist elastic may be applied to the elastic web material along the dividing line in the elastic web material, before forming the cut in the elastic web material and subsequently forming the cut through the elastic web material and through the waist elastic. Thereby, after cutting the elastic web material and shifting position of first body panel web and the tensioned second body panel web, the applied and divided waist elastic will form front and rear waist elastic on the produced pant-type articles.

In a method as disclosed herein comprising a step of dividing the heat-treated elastic web material in two parts, the zones with reduced elasticity which are formed in the elastic web material may each be divided in a first part and a second part by the cut in the elastic web material with the first part of each zone with reduced elasticity being located in the tensioned first body panel web and the second part of each zone with reduced elasticity being located in the tensioned second body panel web.

In a method as disclosed herein comprising a step of dividing the heat-treated elastic web material in two parts, and shifting position of the tensioned first body panel web and the tensioned second body panel web in the cross machine direction, the zones with reduced elasticity which are formed in the elastic web material may have a shape with a first end portion and a second end portion and an intermediate portion between the first end portion and the second end portion, as seen in the cross machine direction, the first end portion and the second end portion having a greater width in the machine direction than a width in the machine direction of the intermediate portion, the cut in the elastic web material dividing each zone with reduced elasticity in the intermediate portion of the zone with reduced elasticity.

In a method as disclosed herein comprising a step of dividing the heat-treated elastic web material in two parts, the step of arranging the tensioned first body panel web and the tensioned second body panel web side-by-side at a distance from each other in the cross machine direction may involve pulling the tensioned first body panel web apart from the tensioned second body panel web in the cross machine direction, whereby the first side edge of the tensioned first body panel web forms the first waist edge of the composite web of precursor articles and the first side edge of the tensioned second body panel web forms the second waist edge of the composite web of precursor articles. Waist elastic may be applied along the first and second side edges of the elastic web material before or after forming the cut in the elastic web material.

In a method as disclosed herein comprising a step of dividing the heat-treated elastic web material in two parts, and pulling the parts apart in the cross machine direction, the zones with reduced elasticity which are formed in the elastic web material may have a shape with a first end portion and a second end portion and an intermediate portion between the first end portion and the second end portion, as seen in the cross machine direction the first end portion and the second end portion having a smaller width in the machine direction than a width in the machine direction of the intermediate portion, the cut in the elastic web material dividing each zone with reduced elasticity in the intermediate portion of the zone with reduced elasticity.

Generally, waist elastic may be applied to a waist edge of the tensioned first body panel web and to a waist edge of the tensioned second body panel web before forming the composite web of precursor articles or may be applied along the first and second waist edges of the composite web of precursor articles.

In a method of producing a disposable pant-type article as disclosed herein, an absorbent assembly being attached to the first and second body panel webs and bridging the distance between the first and second body panel webs may form the only connections between the first and second body panel webs in the coherent composite web of precursor articles. Leg opening portions are formed in the coherent composite web of precursor articles in the gaps between the intermittently attached absorbent assemblies. The leg opening portions may subsequently be shaped by cutting to provide a desired curvature to the leg opening edge.

Alternating crotch portions and leg opening portions in a coherent chassis web are formed by cutting out leg openings in a chassis web which has been formed by continuous connection of the inwardly facing side edges of the first and second panel webs. The side edges of the first and second panel webs may either be directly connected with each other or may be indirectly connected by means of a bridging web.

As set out herein, the distance between the first and second body panel webs may be bridged by an outer or inner cover web which is applied over the full cross machine direction width of the composite web of precursor articles, or which is applied at least over the crotch region and optionally over all or a portion of one or both of the first and second body panel webs. In such case, leg openings must be cut out between the intermittently applied absorbent assemblies. The absorbent assemblies may be applied before or after forming the leg openings.

The elastic panel web may include reinforcing elastic elements, such as leg elastic elements and/or waist elastic elements which are applied in addition to a coherent elastic layer in the elastic panel web.

As set out herein, waist elastic is preferably applied after the zone or zones with reduced elasticity have been created in the elastic web material.

The method as disclosed herein may further involve applying components such as leg elastic, elastic barrier cuffs, disposal means, fastener elements, etc. Such components will then form part of a disposable absorbent pant-type article as disclosed herein.

As set out herein one or both of the front panel web and the rear panel web may comprise or consist of a tri-laminate web comprising two outer nonwoven layers and an intermediate coherent elastic layer, such as an elastic film or an elastic nonwoven sandwiched between the outer nonwoven layers. A three-layer nonwoven-film-nonwoven laminate provides elastic panels with smooth, soft and skin-friendly textile-like outer and inner surfaces. The laminate may be produced by any known method or combination of methods such as stretch-bonding methods, methods involving incremental stretching, etc.

The layers of the laminate may be bonded together by a pattern of discrete bonding elements, such as point bonds, which are distributed over the surface of the laminate. The bonding elements may be formed by ultrasonic bonding, or heat bonding, as set out herein. After severing individual pant-type articles from a production web, the tensioned elastic layer in the laminate contracts and causes the non-elastic nonwoven layers to pucker between the bonding elements, whereby the bulkiness of the outer surface of the laminate is increased in the finished pant-type article. As set out herein, bonding of the laminate may also be performed such that apertures are formed in the elastic layer at or in the bonding elements, thereby increasing breathability of the laminate. Such apertures in the inner elastic layer in a three-layer laminate are generally not visible from the surfaces of the outer layers of the laminate.

A three-layer elastic panel web may be formed by stretch-bonding a first surface of an elastic layer, such as an elastic film or an elastic nonwoven to a first nonwoven layer and subsequently bonding a second nonwoven layer to a second surface of the elastic layer. As set out herein, bonding between the layers may be carried out by ultrasonic bonding, or heat bonding.

As set out herein, in addition to the coherent elastic layer, the elastic panel web may include reinforcing elastic elements which may be applied between the first and second nonwoven layers or which may be applied to an outer surface of the three-layer panel web. Forming a laminate by stretch bonding implies that the elastic layer is stretched, such as by 50 to 600% in the machine direction MD and held in the stretched state while being bonded to a non-elastic or less elastic web such as a non-elastic or less elastic nonwoven layer, to retain the elastic properties of the elastic layer in the laminate. As set out herein, the first and second nonwoven layers are preferably non-elastic nonwoven layers.

When using laminate elastic panel webs comprising a stretch-bonded elastic layer and one or more non-stretchable layers, such as one or more non-stretchable nonwoven layers in the method as disclosed herein, the webs are held tensioned, throughout the process up until the final step of severing individual pant-type articles from the chassis web. This generally means that the webs are stretched in the machine direction to the maximum extent permitted by the non-stretchable layer or layers.

A crotch web as disclosed herein may be any suitable non-stretchable web material, such as a non-stretchable nonwoven web, a non-stretchable polymer film or a non-stretchable laminate. Laminates comprising one or more nonwoven webs and laminates comprising one or more nonwoven webs and a polymer film are also conceivable. In a crotch web forming an outer garment-facing surface of the pant-type article, it may be preferred that the outer garment-facing surface is formed by a nonwoven material. The crotch web may be a crotch panel web having a first side edge and an opposing second side edge, the first side edge of the crotch panel web being attached in a front seam to the front crotch edge of a tensioned front panel web and the second side edge of the crotch panel web being attached in a rear seam to the rear crotch edge of a tensioned rear panel web, thereby bridging a gap between the front crotch edge of the front panel web and the rear crotch edge of the rear panel web. Alternatively, the crotch web may be an outer or inner cover web extending in the cross machine direction the full distance or at least 75% of the distance between the front waist edge and the rear waist edge of the composite web of precursor articles.

BRIEF DESCRIPTION OF THE DRAWINGS

The absorbent articles and the method for their production as disclosed herein will be further explained hereinafter with reference to the appended drawings wherein.

DETAILED DESCRIPTION

Different aspects of the present disclosure will be described more fully hereinafter with reference to the enclosed drawings. The embodiments disclosed herein can be realized in many different forms and should not be construed as being limited to the aspects set forth herein.

The absorbent pant-type article may be a baby diaper, a training pant, a feminine hygiene pant, swimwear, disposable underpants, etc.

The drawings are schematic and the pant-type article which is shown in the figures is a simplified article. It is to be understood that the article may contain further features, such as barrier cuffs, disposal means, etc. It is also to be understood that the waist elastic disclosed herein is optional or that any other suitable type of waist elastic may be used. The side seams may be reclosable side seams, and the pant-type article may be provided with fastener elements to provide reclosability of the side seams.

The method for producing a pant-type article as disclosed herein is described in the context of a disposable pant-type article comprising an absorbent assembly. However, it is to be understood that the method is equally applicable to the production of absorbent pant-type articles which do not comprise a pre-fabricated absorbent assembly. The method as disclosed herein is useful in the production of any type of disposable pant-type article, such as adult incontinence articles, baby diapers, training pants, swim-pants, disposable underpants, sanitary pants for feminine use, etc.

Figure 1:
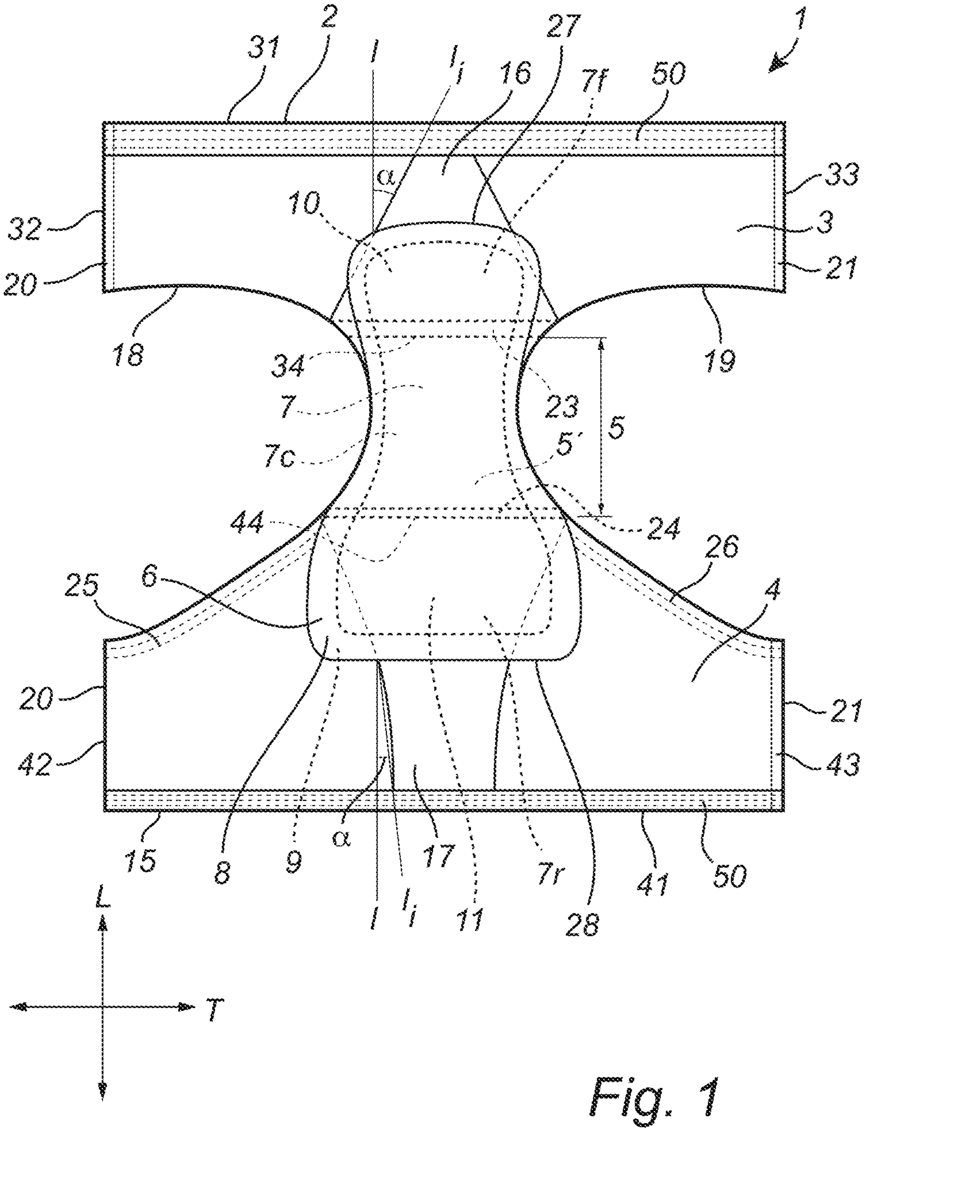
FIG. 1 shows a planar view of a stretched-out absorbent pant-type article with an absorbent assembly and with open side seams, as seen from an inner surface of the pant-type article.
Figure 2:
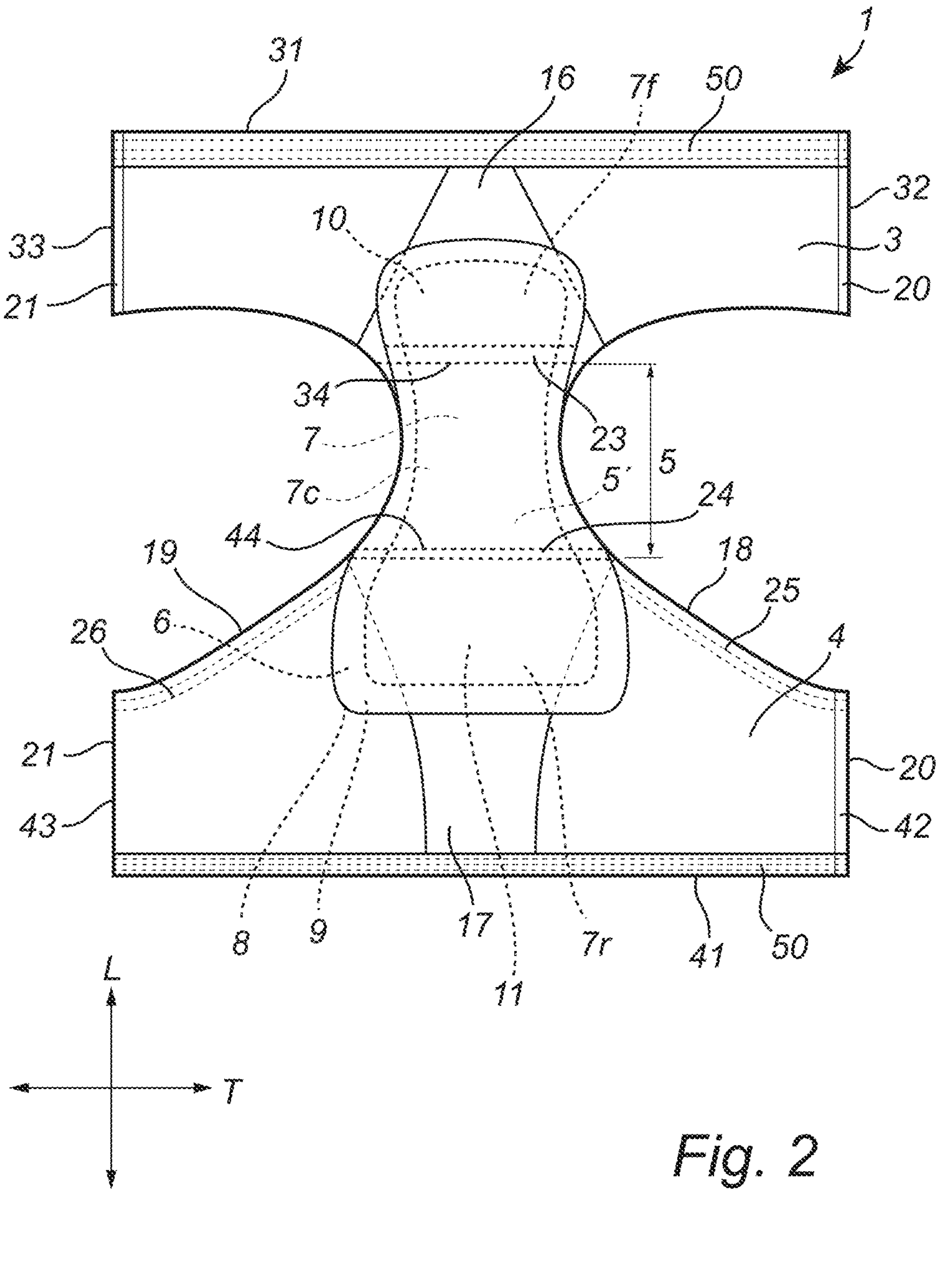
FIG. 2 shows a planar view of the stretched-out absorbent pant-type article in FIG. 1, as seen from an outer surface of the pant-type article.

With initial reference to FIGS. 1 and 2, there is shown a disposable absorbent pant-type article 1 in the form of a pant-type incontinence article for adult users. The pant-type article 1 is shown in FIGS. 1 and 2 in an unfolded and flat condition with all elastic elements and components in an extended state, such that the pant-type article 1 appears generally two-dimensional. FIG. 1 shows the article from an inner, wearer-facing surface of the article and FIG. 2 shows the article from an outer, garment-facing surface of the article.

The pant-type article has 1 a longitudinal direction L and a transverse direction T. Any measurements of distances and dimensions are made with the pant-type article in the fully stretched-out, non-gathered condition as shown in FIGS. 1 and 2.

The article comprises a front body panel 3 which is constituted by a front body panel material which is elastically stretchable in the transverse direction T and a rear body panel 4, which is constituted by a rear body panel material which is elastically stretchable in the transverse direction T. A crotch region 5 is located between the front body panel 3 and the rear body panel 4.

The front body panel web which is elastically stretchable at least in the transverse direction T provides the overall elastic stretchability of the front body panel 3.

The rear body panel web which is elastically stretchable at least in the transverse direction T provides the overall elastic stretchability of the rear body panel 4.

The article further comprises an absorbent core 7. The absorbent core 7 forms part of an absorbent assembly 6 which is arranged in the crotch region 5 of the pant-type article 1 and which extends in the longitudinal direction L forward in over the front body panel 3 and rearward in over the rear body panel 4. The absorbent assembly 6 bridges a gap between the front and rear body panels 3, 4. The absorbent assembly 6 which is shown in FIGS. 1 and 2, is a separately produced component which comprises the absorbent core 7, a liquid permeable topsheet 8 and a liquid impermeable backsheet 9. The absorbent core 7 is sandwiched between the topsheet 8 and the backsheet 9.

The absorbent core 7 is arranged with a central part **7*c* of the absorbent core 7 located in the crotch region 5, a front end part 7*f* of the absorbent core overlapping with the front body panel 3 in a front overlap area 10 and a rear end part 7*r* of the absorbent core 7 overlapping with the rear body panel 4 in a rear overlap area 11**.

The absorbent core 7 which is shown in the figures has an hourglass shape. However, the disclosure is not limited to hourglass shaped cores, and it is to be understood that the absorbent core may have any useful shape, such as rectangular shape T-shape, etc., as known in the art.

The absorbent assembly 6 is applied on the inner surface of the pant-type article 1, the inner surface being the surface which is intended to be facing the wearer when the pant-type article 1 is being worn. The inner surface of the absorbent assembly 6 is formed by the liquid permeable topsheet 8 and may optionally include barrier cuffs (not shown) extending along the side edges of the absorbent assembly 6.

As disclosed herein, the topsheet 8 and the backsheet 9 may both extend beyond the periphery of the absorbent core 7 and may be joined to each other in an edge seal extending along the periphery of the absorbent core 7 outward of a peripheral edge of the absorbent core 7. Furthermore, a peripheral edge portion of the absorbent assembly 6 may be formed by only one of the topsheet and the backsheet, An absorbent core 7 as disclosed herein may comprise any conventional material suitable for absorbing discharged bodily wastes, such as cellulosic fluff pulp, tissue layers, highly absorbent polymers (super absorbents), absorbent foam materials including hydrogel-foam material, absorbent nonwoven materials, or the like. The absorbent core can comprise non-absorbent components such as stiffening elements, shaping elements, binders, etc. Various types of liquid-receiving and liquid distribution elements can also be included in the core.

The absorbent core 7 may be a three-dimensionally shaped core with different amounts of absorbent material in different parts of the core, and may be provided with features such as embossings, fluid acquisition cavities and fluid distribution channels. Properties of the absorbent core such as density, amount of absorbent material and absorbent capacity may also be varied in different portions of the absorbent core. The absorbent core 7 may comprise a core cover, sandwiching absorbent material between an upper core cover layer and a lower core cover layer. Such core cover may be a tissue material or a nonwoven material and is provided in addition to a topsheet and a backsheet.

The liquid permeable topsheet 8 may comprise or consist of a nonwoven material. Other suitable topsheet materials include tow fibres, porous foams, apertured plastic films and laminates and combinations of such materials. The materials which are best suited as topsheet materials are soft and non-irritating to the skin, are readily penetrated by body fluids, and display low rewet.

The liquid impermeable backsheet 9 may consist of a thin plastic film, e. g. a polyethylene or polypropylene film, a nonwoven material coated with a liquid impervious material, a hydrophobic nonwoven material which resists liquid penetration or laminates of plastic film and nonwoven. The backsheet material may be breathable to allow vapour to escape from the absorbent body, while still preventing liquids from passing through the backsheet material.

The topsheet and backsheet may be connected to each other for example by adhesive bonding, gluing or welding by heat or ultrasonically. The topsheet and/or the backsheet may further be attached to the absorbent core by any method known in the art, such as adhesive, heat-bonding, welding, needling, etc.

The front body panel 3 has a front panel waist edge 31 extending in the transverse direction T, a pair of front panel side edges 32, 33 extending in the longitudinal direction L and a front panel crotch edge 34 extending in the transverse direction T opposite the front panel waist edge 31. The rear body panel 4 has a rear panel waist edge 41 extending in the transverse direction T, a pair of rear panel side edges 42, 43 extending in the longitudinal direction L and a rear panel crotch edge 44 extending in the transverse direction T opposite the rear panel waist edge 41.

The crotch region 5 comprises a crotch region web, preferably a non-stretchable web material, such as a non-stretchable nonwoven.

Figure 3:
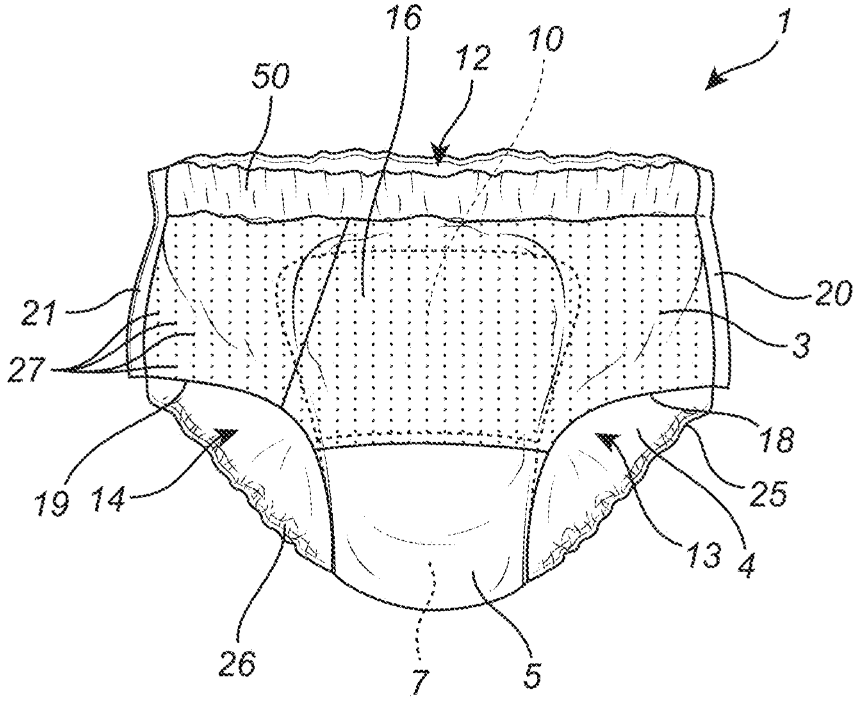
FIG. 3 shows the pant-type article in FIGS. 1 and 2 in a non-stretched condition.

In the pant-type article 1 which is shown in FIGS. 1-3, the crotch region 5 is comprises a crotch panel 5' which is attached to the front body panel 3 in a front overlap seam 23 extending along the front panel crotch edge 34, and which is attached to the rear body panel 4 in a rear overlap seam 24 extending along the rear panel crotch edge 44. The crotch panel 5' is preferably formed from a non-stretchable web material such as a non-stretchable nonwoven.

Alternatively, or in addition to applying a crotch panel in the crotch region as shown in FIGS. 1-3, the crotch region may comprise a portion of a web material, such as an inner or outer cover web material of the pant-type article which extends continuously in the longitudinal direction from the front panel waist edge to the rear panel waist edge and bridges a gap between the front panel crotch edge and the rear panel crotch edge. The portion of the continuous cover web material which is applied in the crotch region between the front panel crotch edge and the rear panel crotch edge constitutes a crotch web material.

In the pant-type article 1 shown in the figures, the elastically stretchable front body panel 3 has been formed from a continuous front body panel web which has been applied in a machine direction MD corresponding to the transverse direction T of the pant-type article 1. The front body panel web thereby extends in the transverse direction T across the pant-type article 1 from the first front panel side edge 32 to the second front panel side edge 33 and extends in the longitudinal direction L from the front waist edge 31 to the front crotch edge 34. The elastically stretchable rear body panel 4 has been formed from a continuous rear body panel web which has been applied in a machine direction MD corresponding to the transverse direction T of the pant-type article 1. The rear body panel web thereby extends in the transverse direction T across the pant-type article 1 from the first rear panel side edge 42 to the second rear panel side edge 43 and extends in the longitudinal direction L from the rear waist edge 41 to the rear crotch edge 44.

The crotch region 5 is arranged between the front body panel 3 and the rear body panel 3 and is contiguous with the front body panel 3 along the front panel crotch edge 34 and is contiguous with the rear body panel 4 along the rear panel crotch edge 44. The extension of the crotch region 5 in the longitudinal direction L is defined as the distance in the longitudinal direction between the front panel crotch edge 34 and the rear panel crotch edge 44.

The first front panel side edge 32 is intended to be joined to the first rear panel side edge 42 in a first side seam 20 and the second front panel side edge 33 is intended to be joined to the second rear panel side edge 43 in a second side seam 21 to form a pant-type article 1 having a waist opening 12, a first leg opening 13 and a second leg opening 14, as shown in FIG. 3.

The waist opening 12 is defined by the front panel waist edge 31 and the rear panel waist edge 41. A first leg edge 18 defines the first leg opening 13 and a second leg edge 19 defines the second leg opening 14.

The side seams of a pant-type article as disclosed herein may be generally band-shaped joins which are formed by ultrasonic welding or thermowelding. To have sufficient strength to withstand the forces to which the pant-type article is exposed during donning of the article and to allow sufficient production tolerances when cutting off individual pant-type garments from a precursor web, the side seams commonly have a width in the order of 5 to 10 millimetres. It is also known to make side seams having a width of less than 5 mm.

It is generally desired that a soiled pant-type garment can be easily removed without having to pull the garment down over the legs of a user. Therefore, the side seams are commonly made such that they are breakable by manual force to allow a user or a caregiver to pull apart the side seams before removing a soiled pant-type garment. The pant-type article may be a reclosable article which means that the side seams can be manually opened e.g., to check if the article is soiled and needs to be changed and then closed again if the article is found to still be in a condition allowing further use. Reclosability is commonly provided by means of fastener elements, such as hook-and-loop-type fasteners.

The disposable pant-type article 1 comprises a front body panel zone with reduced elasticity 16, the front body panel zone with reduced elasticity 16 being arranged in the overlap area 10 between the absorbent core 7 and the front body panel 3.

The disposable pant-type article 1 which is shown in FIGS. 1-3 also comprises a rear body panel zone with reduced elasticity 17, the rear body panel zone with reduced elasticity 17 being arranged in the overlap area 11 between the absorbent core 7 and the rear body panel 4. As is shown in FIGS. 1 and 2, both the front body panel zone with reduced elasticity 16 and the rear body panel zone with reduced elasticity 17 are arranged in the corresponding overlap area 10,11 between the absorbent core 7 and the body panel 3,4, with the body panel zone with reduced elasticity 16,17 having a tapering shape in the longitudinal direction L of the disposable pant-type article 1. The extension of the front body panel zone with reduced elasticity 16 in the transverse direction T adjacent the waist opening 12 is smaller than the extension of the front body panel zone with reduced elasticity 16 in the transverse direction T adjacent the crotch region 5. Furthermore, in the absorbent pant-type article 1 which is shown in FIGS. 1-3, the extension of the rear body panel zone with reduced elasticity 17 in the transverse direction T adjacent the waist opening 12 is smaller than the extension of the rear body panel zone with reduced elasticity 17 in the transverse direction T adjacent the crotch region 5. The extension in the transverse direction T of a body panel zone with reduced elasticity 17 is also referred to herein as the width of the body panel zone with reduced elasticity. It is not essential to the pant-type absorbent articles as disclosed herein that both the front body panel zone with reduced elasticity 16 and the rear body panel zone with reduced elasticity 17 has a tapering shape with a smaller width at the waist opening 12 than at the crotch region 5. If both a front body panel zone with reduced elasticity 16 and a rear body panel zone with reduced elasticity 17 are provided, it is sufficient that only one of the front body panel zone with reduced elasticity 16 and the rear body panel zone with reduced elasticity 17 has the tapering shape. If only one body panel zone with reduced elasticity has a tapering shape, it may be preferred that the tapering shape be provided to the front body panel zone with reduced elasticity 16.

The front and rear body panel zones with reduced elasticity 16, 17 which are shown in FIGS. 1-3 have a tapering shape in the longitudinal direction L of the disposable pant-type article, with a wider portion at the crotch region 5 and a narrower portion at the waist elastic feature 50. By forming zones with reduced elasticity having a narrower part at the waist portion of the article and a broader part at the crotch portion of the article, the elasticity in the front and rear body panels 3, 4 is higher at the waist portion causing the side seams to assume the inwardly sloping configuration shown in FIG. 3. The shaped side seams conform better to the shape of the hips of a wearer of the article than the side seams of a regular pant-type absorbent article and improves fit and stay-up properties of the pant-type absorbent article.

The front and rear body panel zones with reduced elasticity 16, 17 are shown in the figures to be arranged such that they substantially coincide with the overlap areas 10 11, between the absorbent core 7 and the front and rear body panels 3,4. It may be preferred that a body panel zone with reduced elasticity coincides with a corresponding front or rear overlap area 10, 11 to at least 70%, more preferred to at least 80%.

The front and rear body panel zones with reduced elasticity 16, 17 are shown in the figures to be arranged such that they substantially coincide with the overlap areas 10 11, between the absorbent core 7 and the front and rear body panels 3,4. It may be preferred that a body panel zone with reduced elasticity coincides with a corresponding front or rear overlap area 10, 11 to at least 70%, more preferred to at least 80%. The front and rear body panel zones with reduced elasticity 16, 17 may be shaped and sized to correspond to the shape and size of the respective one of the front and rear overlap areas 10,11.

The tapering part of the front body panel zone with reduced elasticity 16 which is located between the forward end edge of the absorbent assembly 6 and the front end edge of the front body panel 3, is the part of the front body panel zone with reduced elasticity 16 that provides the pant-type absorbent article 1 with an improved body-conforming shape by creating an elastic gradient which causes the side seams 20, 21 to assume the sloping configuration shown in FIG. 3.

As shown in FIG. 1, a tapering angle a is measured between a line of inclination $I_i$ of the portion of the front body panel zone with reduced elasticity 16 which is located between the forward end edge 27 of the absorbent assembly 6 and the front waist edge 2 of the front body panel 3, and a line $I_l$ which is parallel to the longitudinal direction L of the pant-type absorbent article 1. The tapering angle a of the front body panel zone with reduced elasticity 16 may be from 3° to 35°, preferably from 7° to 25°.

In articles where the absorbent assembly is narrower than the front body panel zone with reduced elasticity, such that the front body panel zone with reduced elasticity extends in the transverse direction beyond the side edges of the absorbent assembly, the line of inclination is drawn from a point where the front body panel zone with reduced elasticity intersects with a line which is parallel to the transverse direction T of the pant-type absorbent article, and which is drawn through a forward end point of the absorbent assembly; to a point where the front body panel zone with reduced elasticity intersects with the front waist edge of the front body panel.

In a corresponding manner the tapering angle a of the rear body panel zone with reduced elasticity 17 is measured between a line of inclination $I_i$ of the portion of the rear body panel zone with reduced elasticity 17 which is located between the rearward end edge 28 of the absorbent assembly 6 and the rear waist edge 15 of the rear body panel 4, and a line $I_l$ which is parallel to the longitudinal direction L of the pant-type absorbent article 1. The tapering angle a of the rear body panel zone with reduced elasticity 17 may be from 3° to 35°, preferably from 7° to 25°.

In articles where the rear part of the absorbent assembly is narrower than the rear body panel zone with reduced elasticity, such that the rear body panel zone with reduced elasticity extends in the transverse direction beyond the side edges of the absorbent assembly, the line of inclination is drawn from a point where the rear body panel zone with reduced elasticity intersects with a line which is parallel to the transverse direction T of the pant-type absorbent article, and which is drawn through a rearward end point of the absorbent assembly; to a point where the rear body panel zone with reduced elasticity intersects with the rear waist edge of the rear body panel.

When the edge of the body panel zone with reduced elasticity deviates from a straight line, as is the case with the funnel-shaped rear body panel zone with reduced elasticity 17 shown in the figures, the line of inclination $I_i$ is drawn from the point where the inclined edge of the body panel zone with reduced elasticity crosses the end edge of the absorbent assembly 6 to the point on the end edge of the body panel where the inclined edge of the body panel zone meets the end edge of the body panel.

In the example shown in the figures, the front waist edge 2 of the front body panel 3 coincides with the front waist edge 31 of the pant-type absorbent article 1 and the rear waist edge 15 of the rear body panel 4 coincides with the rear waist edge 41 of the pant-type absorbent article 1, as the elastic waist feature 50 is applied such that it completely overlaps the front and rear body panels 3,4. As set out herein, an elastic waist feature may alternatively be applied to the absorbent pant-type article such that the elastic waist feature extends 4 in the longitudinal direction L beyond the waist edges of the front and rear body panels 3, 4.

In absorbent pant-type articles in which the absorbent core has been applied without being incorporated into an absorbent assembly the line of inclination $I_i$ is determined for the portion of the body panel zone with reduced elasticity which is located between the end edge of the absorbent core and the waist edge of the body panel.

The disposable pant-type article which is shown in FIGS. 1-3 may alternatively have a body panel zone with reduced elasticity in only one of the front body panel 3 and the rear body panel 4. In case the disposable pant type article has only a single body panel zone with reduced elasticity, it may be preferred that the body panel zone with reduced elasticity is a front body panel zone with reduced elasticity. A front body panel zone with reduced elasticity may be particularly beneficial, as the front body panel zone with reduced elasticity will be the portion of the pant-type article 1 which is applied over a wearer's belly. The front body panel zone with reduced elasticity 16 will exert less pressure on the wearer's belly, than adjoining, non-treated, portions of the front body panel 3, thereby contributing to improved wearer comfort, while still holding the pant-type article 1 in contact with the wearer's body also in the belly-area.

As disclosed herein, the elastically stretchable front body panel 3 and/or the elastic rear body panel 4 may consist of a single layer of elastic material, preferably an elastic nonwoven material. Alternatively, the elastic front body panel 3 and/or the elastic rear body panel 4 may comprise or consist of an elastic laminate comprising at least a first layer of nonwoven material, and an elastic layer. The elastic laminate may comprise a second layer of nonwoven material, the elastic layer being an intermediate elastic layer arranged between the first and second layers of nonwoven material. One or both of the first and second layers of nonwoven material may be non-elastic nonwoven materials.

The elastic layer in the elastic laminate may comprise or consists of a layer of elastic film, an elastic nonwoven material or an elastic scrim.

At least two layers of the elastic laminate may be bonded together with a plurality of discrete bonding elements 27, the bonding elements 27 being arranged in a bonding pattern, as shown in FIG. 3. The bonding pattern is visible on the full external surface of the elastic front body panel 3 including the front body panel zone with reduced elasticity 16. The bonding pattern is the same over all of the front body panel 3, providing the surface of the front body panel 3 with a uniform appearance, such that the front body panel zone 16 with reduced elasticity is not discernible to the naked eye and that the presence of an absorbent core beneath the front body panel zone with reduced elasticity 16 is obscured. Each discrete bonding element may have a surface area in the order of 0.1 $mm^2$ to 3.0 $mm^2$. It may be preferred that the surface area of the individual bond areas is in the lower part of the range, such as from 0.1 $mm^2$ to 1.5 $mm^2$ or from 0.1 $mm^2$ to 1.0 $mm^2$.

The total bond area may be in the range of from 4% to 13%, preferably in the range of from 5% to 10%.

As disclosed herein, apertures may be arranged in the elastic layer, in or at the bond elements.

In FIG. 3, only the front body panel 3 is visible. However, the rear body panel 4 is preferably also constituted by an elastic laminate having a bonding pattern applied over the full outer surface of the rear body panel 4, the bonding pattern obscuring the presence of the rear body panel zone with reduced elasticity 17 and the portion of the absorbent core 7 which is located inside the rear body panel zone with reduced elasticity 17 in the same way as for the front body panel 3.

Leg elastic members 25, 26 are arranged on the elastically stretchable rear body panel 4 along rear parts of the leg edges 18, 19. Although not shown in the Figures, leg elastic may be applied along other parts of the leg edges 18, 19, such as along the parts of the leg edges 18, 19 extending in the crotch region 5 and/or along the leg edges 18, 19 extending on the front body panel 3. Each leg elastic member may comprise multiple individual elastic elements, such as 2 to 15 individual elastic elements, 3 to 12 individual elastic element or 4 to 10 individual elastic elements.

The multiple individual elastic elements may be elastic strings, threads or bands which are applied spaced apart along the rear leg edge sections of the first and second leg edges.

The reinforcing leg elastic members may be covered with a nonwoven covering web.

The leg elastic members constitute reinforcing elastic which is applied in addition to the elastic material in the front and rear body panel webs. Reinforcing leg elastic members are optional to the pant-type absorbent articles as disclosed herein and may be omitted, such that the only elastification provided at the leg openings 13, 14 is the elasticity from elastically stretchable front and rear body panel materials.

The pant-type article 1 as disclosed herein may have an elastic waist feature 50 arranged along the waist opening 12, as shown in FIGS. 1-3. An elastic waist feature 50 may include one or more elastic elements extending parallel with the front panel waist edge 31 and the rear panel waist edge 41. The elastic waist element or elements may be incorporated in the front body panel 3 and the rear body panel 4 or may be applied as a separate waistband which is attached to the front panel waist edge 31 and the rear panel waist edge 41 or which is attached to the front and/or to the rear body panel 3, 4 with the waistband completely overlapping with the corresponding body panel 3, 4 and sharing a common waist edge. The pant-type article 1 which is shown in FIGS. 1-3 has an elastic waist feature 50 which extends around the full circumference of the waist opening 12, thus forming a continuous waist-encircling waistband.

The waist elastic feature 50 constitutes reinforcing elastic which is applied in addition to the elastic material in the front and rear body panel webs.

The elastic material in elastic elements arranged along the leg openings 13, 14 and the waist opening 12 may be any suitable elastic material such as natural or synthetic rubber, thermoplastic elastomers, such as thermoplastic polyurethane or styrene block co-polymers or elastane, also referred as to spandex (polyurethane-polyurea copolymer). The elastic elements may be of the elastane type that is available under the trade name "LYCRA", but any suitable elastic thread may be used. The threads may have a linear mass density, dtex, of about 80-1200 dtex.

The pant-type articles as disclosed herein may be of the kind shown in the Figures and having a two-part chassis with a crotch panel which is connected to the front panel along the front panel crotch edge, and which is connected to the rear panel along the rear panel crotch edge. Alternatively, the pant-type article may have a unitary chassis having a non-elastic outer or inner cover web extending the full distance between the front panel waist edge and the rear panel waist edge, the cover web constituting a non-elastic layer of each of the front panel and the rear panel and constituting the crotch web material in the crotch region of the pant-type article.

As disclosed herein, the elastically stretchable front body panel and the elastically stretchable rear body panel may comprise or consist of a stretchbonded laminated elastic web material. The stretchbonded laminated elastic web material is preferably bonded with a bonding pattern created by ultrasonic bonding or heat bonding and consisting of a plurality of discrete, uniformly distributed bonding elements. The bonding elements may each have a surface area in the order of 0.1 $mm^2$ to 3.0 $mm^2$. It may be preferred that the surface area of the individual bond areas is in the lower part of the range, such as from 0.1 $mm^2$ to 1.5 $mm^2$ or from 0.1 $mm^2$ to 1.0 $mm^2$. The total bond area may be in the range of from 4% to 13%, preferably in the range of from 5% to 10%.

Suitable stretch-bonded laminates may comprise nonwoven material layers or webs such as spunbond, air laid, wet laid, carded, electro spun or meltblown nonwovens. The nonwoven material may be bonded by any suitable technique, such as by needling, hydroentangling, ultrasonic welding, or thermobonding.

The fibers of the nonwoven materials used herein may be man-made fibers, natural fibers or mixtures of man-made and natural fibers. Man-made fibers include mono-component, bi-component and multicomponent fibers of polymers such as polyolefins, polyesters, polyacrylates, etc., as well as regenerated fibers such as viscose fibers and modal fibers. Natural fibres are for instance cellulosic fibres such as pulp fibers, cotton fibers, flax, hemp, etc.

The nonwoven web-materials used in the pant-type articles as disclosed herein may comprise thermoplastic material. The nonwoven web-materials will typically be incorporated in joins and seams in the pant-type article and it is desirable that the nonwoven webs be weldable by heat or by ultrasonic welding processes. Examples of suitable polymers for use in the fibrous nonwoven webs as disclosed herein are polyethylene polypropylene and other polyolefin homopolymers and copolymers and polyesters. The weldable nonwoven webs have a high content of thermoplastic component and preferably contain at least 50% thermoplastic fibres and more preferably at least 80% thermoplastic fibres.

The elastic material used in the front and rear body panels of an absorbent pant-type article as disclosed herein may be a breathable elastic film such as an apertured or microporous elastic film. The elastic film may have a basis weight of between 20 and 80 $g/m^2$, preferably between 20 and 60 $g/m^2$. The elastic web may be of any suitable elastic polymer, natural or synthetic. Some examples of useful materials for the elastic web are low crystallinity polyethylenes, metallocene-catalyzed low crystallinity polyethylenes, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials.

As set out herein, the front and/or rear body panels may be constituted by an elastic laminate comprising an elastic film which is sandwiched between two non-elastic nonwoven layers and formed into a laminate by bonding the layers together with a bonding pattern of multiple discrete bonding elements. The discrete bonding elements may be created in the laminate such that apertures are formed in the elastic film adjacent to the bonding elements and/or in the bonding elements. The discrete bonding elements increase the bulkiness of the laminate, and the apertures provide the elastic laminate with high breathability, thereby contributing to increased wearer comfort.

The basis weight of a stretchbonded elastic laminate web for use as an elastic panel material in an absorbent pant-type article as disclosed herein is preferably between 40 and 100 $g/m^2$, more preferably not more than 90 $g/m^2$.

A continuous method of producing disposable absorbent pant-type articles as disclosed herein will be described with reference to FIGS. 4-9.

Figure 4:
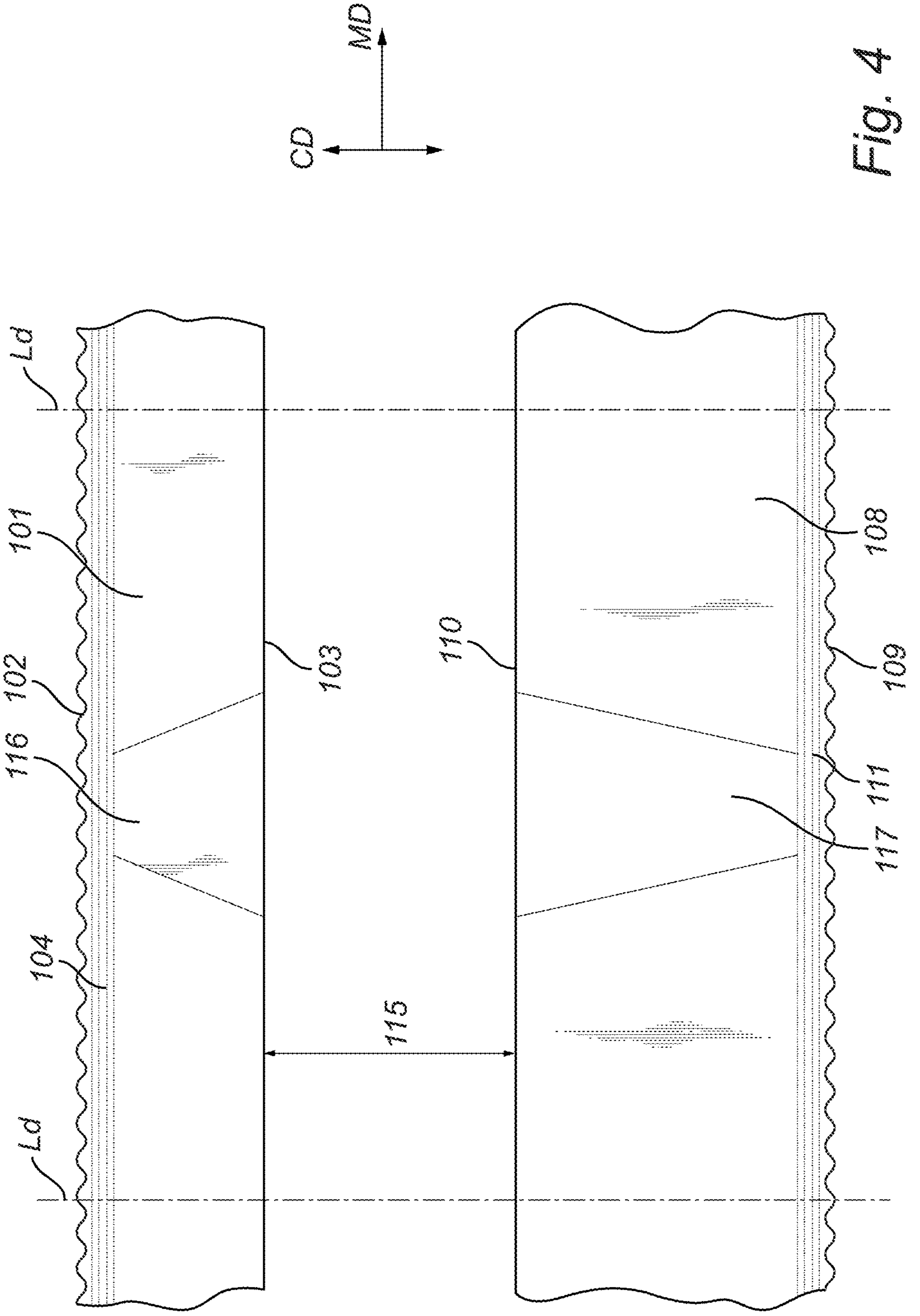
FIG. 4-9 show a planar view of a section of a web of interconnected precursor articles in progressing stages of production.

FIG. 4 shows a continuous elastic front panel web 101 which is being advanced in a machine direction MD. The front panel web 101 is advanced in the machine direction MD while being stretched in the machine direction MD such that the front panel web 101 is tensioned in the machine direction MD.

The front panel web 101 has a front waist edge 102 and an opposing front crotch edge 103.

FIG. 4 further shows a continuous elastic rear panel web 108 which is being fed in the machine direction MD parallel to the elastic front panel web 101. The rear panel web 108 is advanced in the machine direction MD while being stretched in the machine direction MD such that the rear panel web 108 is tensioned in the machine direction MD.

The rear panel web 108 has a rear waist edge 109 and an opposing rear crotch edge 110. The rear panel web 108 is spaced apart from the front panel web 101 in a cross machine direction CD, perpendicular to the machine direction MD, with a distance 115 between the front panel web 101 and the rear panel web 108 in the cross machine direction CD between the crotch edge 103 of the front panel web 101 and the crotch edge 110 of the rear panel web 108.

Front zones 116 with reduced elasticity are formed in the elastic front panel web 101 by exposing portions of the elastic front panel web 101 to heat treatment, the front zones 116 with reduced elasticity being spaced-apart in the machine direction, MD, and having a tapering shape in the cross machine direction CD of the tensioned first body panel web.

Rear zones 117 with reduced elasticity are formed in the elastic rear panel web 108 by exposing portions of the elastic rear panel web 108 to heat treatment, the rear zones 116 with reduced elasticity being spaced-apart in the machine direction, MD, and having a tapering shape in the cross machine direction CD of the tensioned first body panel web.

In the heat treatment step, the heat which is supplied to the elastic web material is preferably controlled to avoid raising the temperature of thermoplastic material in the elastic web material above the melting point of the thermoplastic material. Thereby, the fibrous structure of a nonwoven web comprising or consisting of thermoplastic fibres and forming part of the elastic web material may be retained or at least substantially retained in the elastic web material. The heat supply may be controlled by controlling the heat exposure time and/or the temperature of a heat supply means such as a heating roller.

In the heat treatment step, sufficient heat is supplied to reduce the elasticity of the elastic web material without completely obliterating the elasticity in the elastic web material.

The elastic front panel web 101 and/or the elastic rear panel web 108 may be an elastic laminate web material as disclosed herein. The elastic laminate web material may be formed by bonding at least a first layer of nonwoven material to an elastic layer, bonding being performed with a plurality of discrete bonding elements, the bonding elements being arranged in a bonding pattern, preferably in a bonding pattern of uniformly distributed bonding elements.

The provision of heat-treated zones 116, 117 of reduced elasticity in the both the elastic front panel web 101 and the elastic rear panel web 108 is optional to the method and the pant-type absorbent articles as disclosed herein. If only one of the elastic front panel web 101 and the elastic rear panel web 108 is provided with heat treated zones of reduced elasticity, it may be preferred that the body panel web with reduced elasticity is the elastic front panel web 101.

In the method illustrated in FIGS. 4-9, the elastic front panel web 101 is provided with a front panel zone with reduced elasticity 116 having a shape tapering in a direction from the front crotch edge 103 to the front waist edge 102. It may be preferred that the front panel zone with reduced elasticity 116 is created before application of any waist elastic, such that the heat treatment does not affect waist elastic arranged along the front waist edge 102 of the elastic front panel web 101.

Likewise, the elastic rear panel web 108 is provided with a rear panel zone with reduced elasticity 117 having a shape tapering in a direction from the rear crotch edge 110 to the rear waist edge 109. It may be preferred that the rear panel zone with reduced elasticity 117 is created before application of any waist elastic, such that the rear panel zone with reduced elasticity 117 does not affect waist elastic 111 arranged along the rear waist edge 109 of the elastic rear panel web 108.

By forming zones with reduced elasticity having a narrower part at the waist portion of the article and a broader part adjacent the absorbent core of the article, the article will have stronger elasticity at the waist portion. Furthermore, in the parts of the front body panel and the rear body panel which are located above the corresponding end edge of an absorbent assembly or of an absorbent core, the increasing elasticity in the front panel and/or in the rear panel of the pant-type absorbent article will cause the side seams to assume an inwardly sloping configuration when the pant-type article is in a non-tensioned state. Such shaped side seams conform better to the shape of the hips of a user, especially a female user.

It is to be understood that the shape and size of the zones with reduced elasticity are not limited to the shapes and sizes shown in FIGS. 1-9, but can be varied as disclosed herein, e.g., depending on the size and cut of the pant-type article as well as the size and shape of an absorbent core in the absorbent pant-type article. However, it is preferred that a body panel zone with reduced elasticity, as disclosed herein, has a continuously tapering shape, without any abrupt change in the width of the body panel zone with reduced elasticity in the part of the zone with reduced elasticity which is arranged between the end edge of the absorbent assembly or the absorbent core of the absorbent pant-type article, and the waist edge of the body panel in which the zone with reduced elasticity is arranged.

Front waist elastic 104 is arranged along the front waist edge 102 and rear waist elastic 111 is arranged along the rear waist edge 109. The front and rear waist elastic 104, 111 have been attached to the front panel web 101 and the rear panel web 108 prior to the production step shown in FIG. 4 e.g., by a method as disclosed in WO 2017/044013 A1 and WO 2017/044014 A1. The method in WO 2017/044013 A1 and WO 2017/044014 A1 starts from a base web to which continuous waist elastic is attached, whereafter the base web is cut in two parts along a cutting line extending in the machine direction and severing both the base web and the waist elastic along the cutting line. Dividing the base web in two parts, results in the formation of a first panel web having a first portion of the waistband component attached thereto and a second panel web having a second portion of the waistband component attached thereto. The two web parts are subsequently shifted in the cross machine direction such that the cut edges of the web parts along which the parts of the waist elastic are attached are arranged facing away from each other. When the web parts are further processed in the method as disclosed herein, the cut edge of the first panel web forms the front waist edge 102 of the front panel web 101 and the cut edge of the second panel web forms the rear waist edge 109 of the rear panel web 108 as shown in FIG. 4. The divided waistband component forms the front waist elastic 104 and the rear waist elastic 111 on the respective front panel web 101 and rear panel web 108.

The method which is described in WO 2017/044013 A1 and WO 2017/044014 A1 results in front waist elastic 104 which coincides with the front waist edge 102 of the front panel web 101 and rear waist elastic 111 which coincides with the rear waist edge 109 of the rear panel web 108.

In the example shown in FIGS. 4-9, the front waist edge 102 and the rear waist edge 109 have matching sinusoidal configurations. It is to be understood that the waist edges need not have the undulating configuration shown in FIGS. 4-9 and that any other configuration may be used such as a straight edge as is shown in FIGS. 1-3, a zig-zag edge, etc. Furthermore, it is to be understood that other methods for attaching waist elastic to the front and rear panel webs may be used. The front waist elastic may alternatively be attached with an edge seam along the front waist edge of the front panel web and the rear waist elastic may be attached with an edge seam along the rear waist edge of the rear panel web. In such embodiments, the waist elastics extend in the cross machine direction CD outward of the waist edge of the corresponding panel web. Another conceivable arrangement of waist elastic is to attach the waist elastic slightly inward of the waist edges of the panel webs. In such embodiments, each waist elastic is fully overlapping with the corresponding panel web, with a small edge portion of the panel web extending in the cross machine direction CD a distance in the order of 2 to 15 mm outward of the waist edge of the panel web, the edge portion of the panel web forming a frill border above the waist elastic when the pant-type article is being worn.

Waist elastic which is attached to the front panel web and the rear panel web by other methods than the method disclosed in WO 2017/044013 A1 and WO 2017/044014 A1, may be attached during any suitable stage of the method as disclosed herein or may be attached prior to the stage shown in FIG. 4. It is also to be understood that the waist elastic members as disclosed herein are optional to the method and the disposable pant-type articles as disclosed herein.

The waist elastic members may comprise or consist of any suitable elastic material or elasticated material as known in the art including elastic threads, elastic film, elastic nonwoven and elastic foam. Furthermore, an elastic member may be applied in the form of multiple elongate elastic elements, as a single band of elastic or elasticated material e.g., an elastic laminate. In all instances, the elastic member is a component of a chassis web or a disposable pant-type article as disclosed herein, which is separate and distinct from the elastic material in the front and rear panel webs of the pant-type article such as leg elastic or body elastic.

Figure 5:
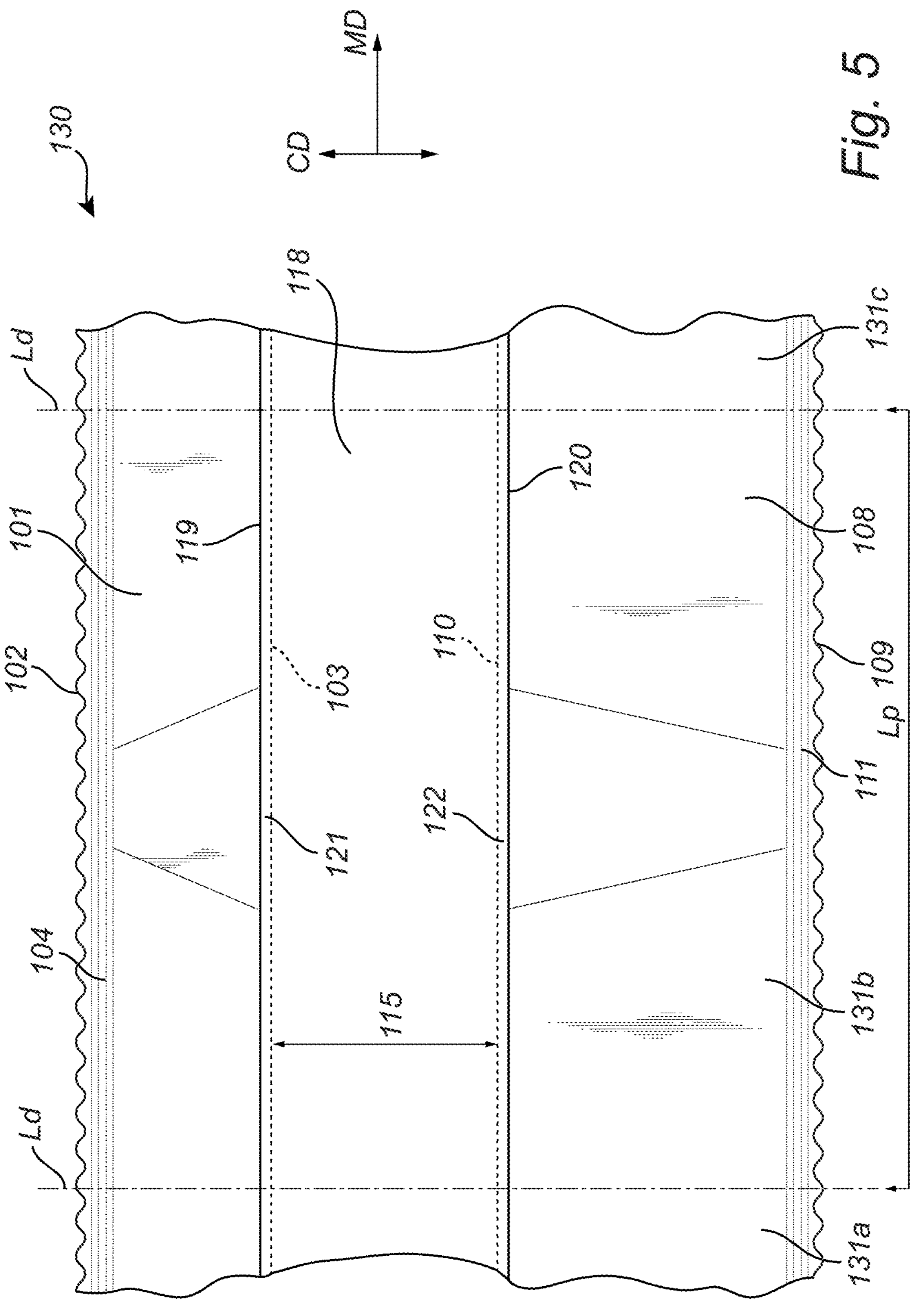

A non-elastic continuous crotch panel web 118 having a first side edge 119 and an opposing second side edge 120 is advanced in the machine direction MD and the first side edge 119 of the crotch panel web 118 is attached in a first overlap seam 121 along the crotch edge 103 of the tensioned front panel web 101 and the second side edge 120 of the crotch panel web 118 is attached in a second overlap seam 122 along the crotch edge 110 of the tensioned rear panel web 108, as shown in FIG. 5. The crotch panel web 118 bridges the distance 115 between the front panel web 101 and the rear panel web 108 to form a coherent composite web 130 of interconnected precursor articles 131*a*, 131*b*, 131*c*, being delimited by dividing lines Ld extending in the cross machine direction CD, each precursor article 131*a*, 131*b*, 131*c* having a pitch-length Lp in the machine direction MD between the dividing lines Ld. The pitch-length Lp of the precursor articles 131*a*, 131*b*, 131*c* remains the same until the final step of the method as disclosed herein, when individual pant-type articles are severed from the chassis web 130 and the tensioning of the composite web 130 of interconnected precursor articles 131*a*, 131*b*, 131*c* ceases.

Figure 6:
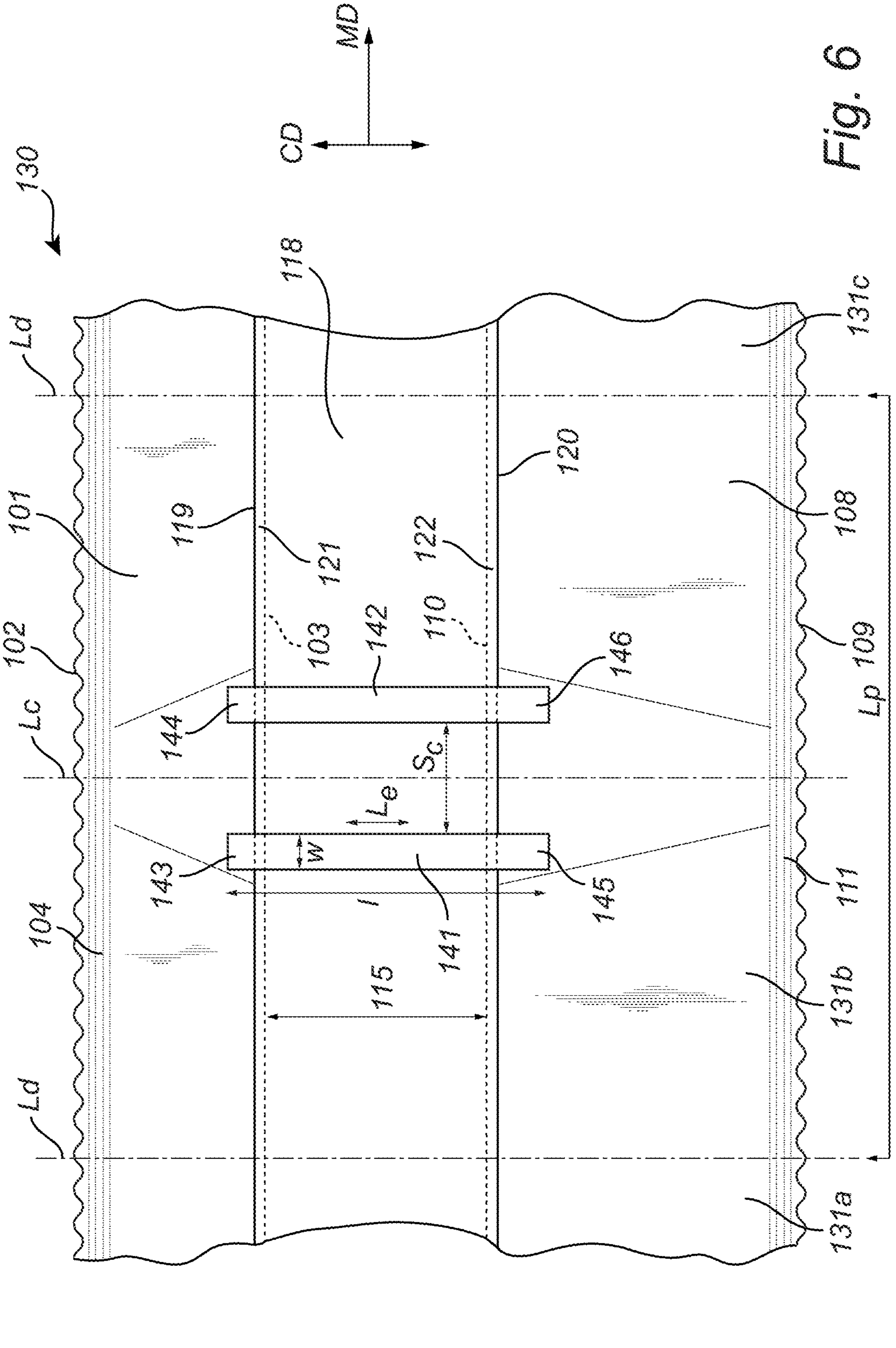

With reference to FIG. 6, a pair of crotch elastic members is provided consisting of a first band-shaped crotch elastic member 141 and a second band-shaped crotch elastic member 142.

Each crotch elastic member 141, 142 is stretched in a longitudinal direction Le of the crotch elastic member coinciding with the cross machine direction CD of the moving composite web 130 of interconnected precursor articles 131*a*, 131*b*, 131*c*.

Each stretched crotch elastic member 141, 142 is attached to the composite web 130 of interconnected precursor articles 131*a*, 131*b*, 131*c* while keeping the crotch elastic member 141, 142 stretched and aligned with the cross machine direction CD. The pair of crotch elastic members 141, 142 is attached to the composite web 130 of interconnected precursor articles 131*a*, 131*b*, 131*c* with the first crotch elastic member 141 being spaced apart from the second crotch elastic member 142 with a crotch spacing Sc in the machine direction and are symmetrically placed on each side of a precursor article centreline Lc extending in the cross machine direction CD. The pairs of crotch elastic members of the precursor articles 131*a*, 131*b*, 131*c* are spaced apart in the machine direction with an article spacing corresponding to the pitch-length of the precursor articles 131*a*, 131*b*, 131*c*.

In the moving composite web 130 of interconnected precursor articles 131*a*, 131*b*, 131*c* which is shown in the Figures, a first end portion 143,144 of each of the first and the second crotch elastic members 141,142 is overlapped with and attached to the tensioned front panel web 101 and a second end portion 145, 146 of each of the first and the second crotch elastic members 141, 142 is overlapped with and attached to the tensioned rear panel web 108, as seen in FIG. 6.

When stretching and applying the stretched crotch elastic members 141, 142 to the chassis web, the first and second end portions 143, 144, 145, 146 of the crotch elastic members 141, 142 may be held in movable clamps in a stretching device (not shown). The clamped end portions 143, 144, 145, 146 are not subjected to stretching and are applied and attached to the composite web 130 of interconnected precursor articles 131*a*, 131*b*, 131*c* in a non-tensioned condition.

The stretched crotch elastic members 141, 142 may have a width was measured in the machine direction MD in the range of from 15 mm to 50 mm and a length I as measured in the cross machine direction in the range of from 150 mm to 350 mm.

The crotch elastic members 141, 142 may comprise or consist of elastic film, or elastic nonwoven bands.

The crotch elastic members are optional to the method and the pant-type absorbent articles as disclosed herein.

Figure 7:
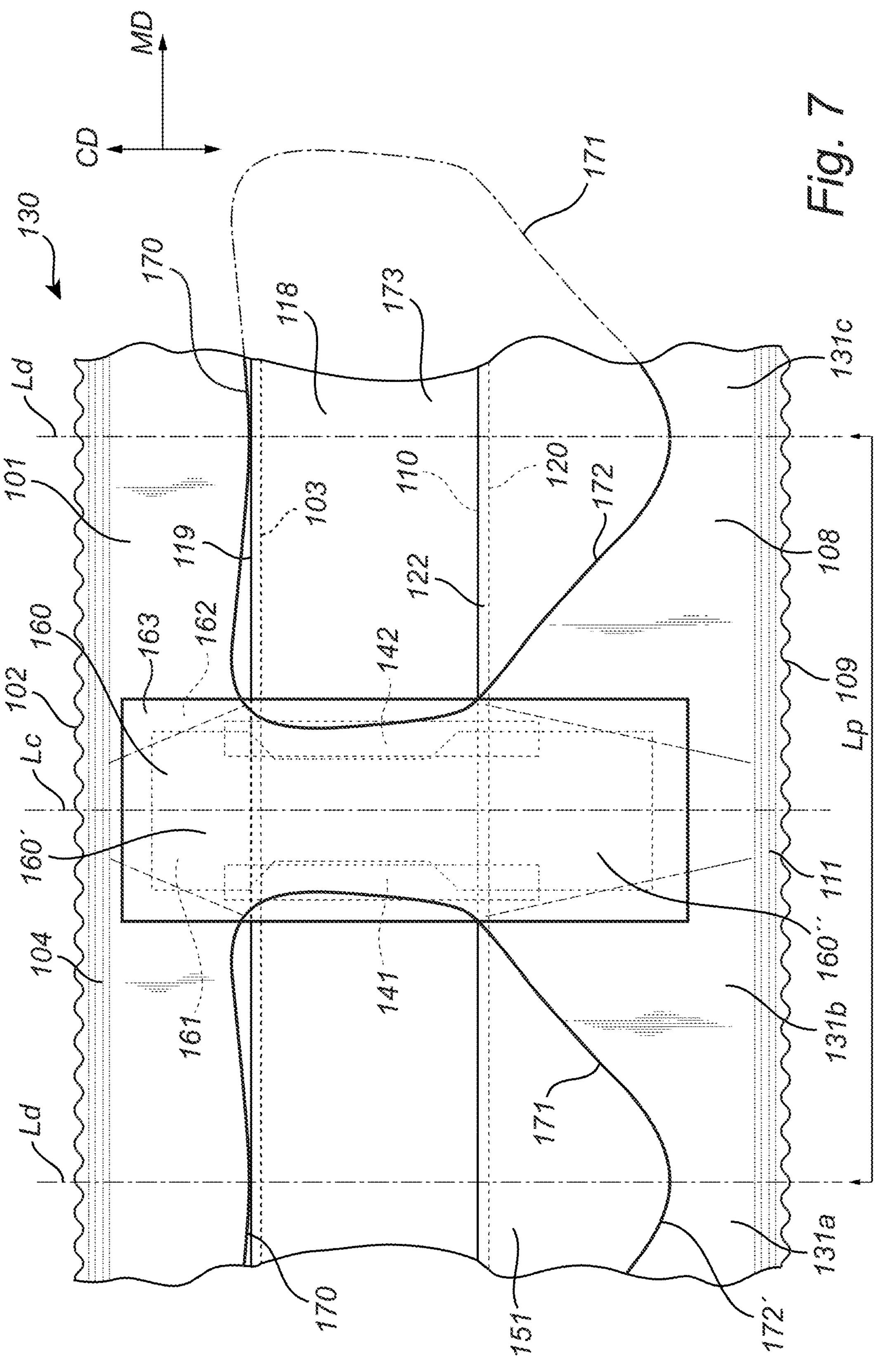
Figure 8:
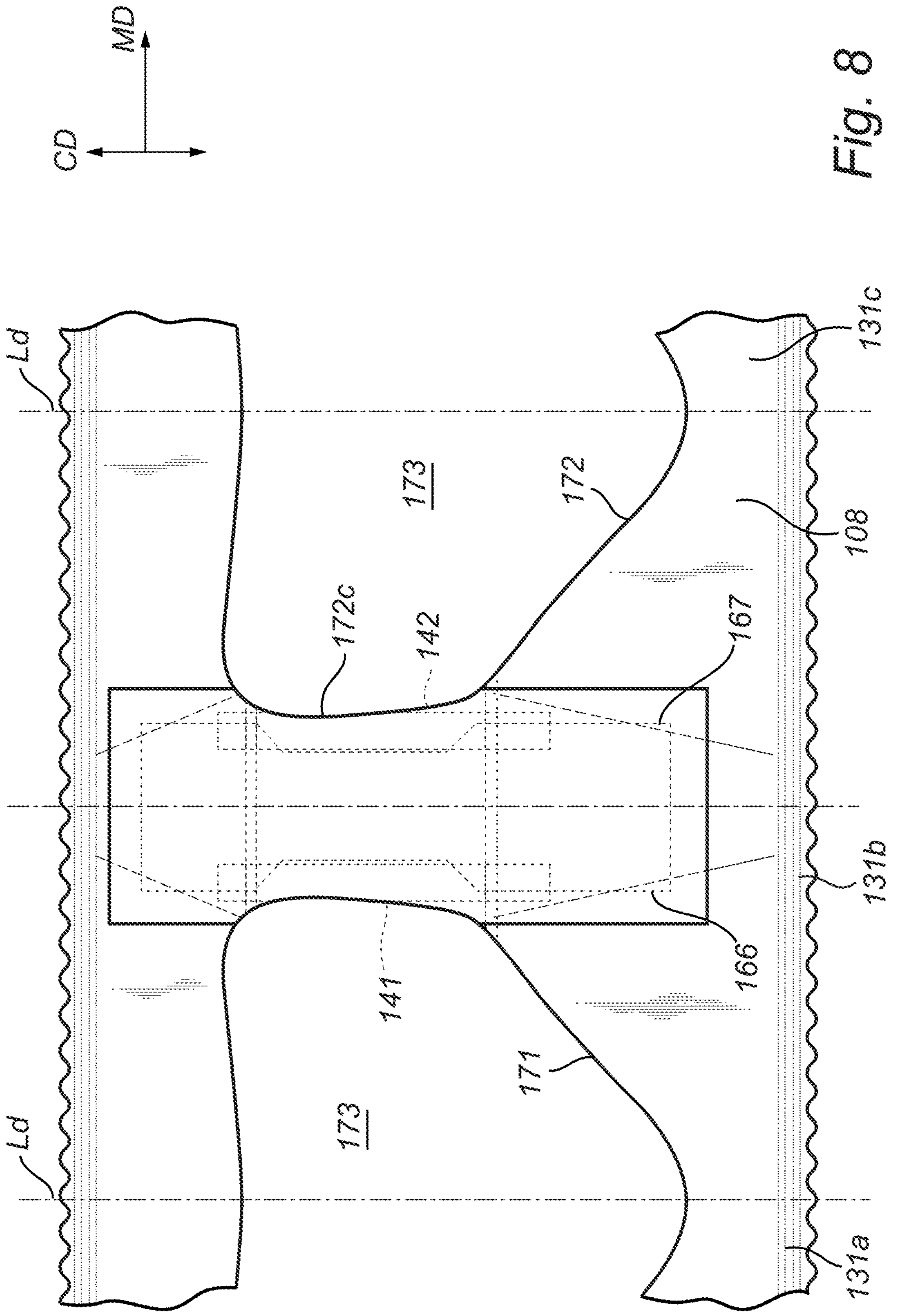

As illustrated in FIG. 7, the method further comprises applying and attaching absorbent assemblies 160 to the moving composite web 130 of interconnected precursor articles 131*a*, 131*b*, 131*c*. Each absorbent assembly 161 comprises an absorbent core 161, a liquid impermeable backsheet 162 and a liquid permeable topsheet 163, the absorbent core 161 being sandwiched between the topsheet 163 and the backsheet 162.

Each absorbent assembly 160 is applied to the composite web 130 of precursor articles on a precursor article centerline Lc extending in the cross machine direction, CD, and covers the stretched and attached crotch elastic members 141, 142.

The absorbent assemblies 160 are applied spaced-apart in the machine direction, MD, and are attached with a front end part 160' of each absorbent assembly 160 overlapping the front zone of reduced elasticity 116 in the front body panel web 101 and a rear end part 160" of the absorbent assembly 160 overlapping the rear panel zone with reduced elasticity 117 in the rear body panel web 108.

The absorbent core 161 is disposed between the topsheet 163 and the backsheet 162 to absorb liquid, such as urine or other bodily fluids, which has passed through the topsheet 163. The topsheet 162, backsheet 163 and the absorbent core 161 may consist of any materials suitable for their purposes.

The absorbent core 161 may be a single-layer structure or may be a layered structure. The absorbent core 161 may comprise suitable amounts of superabsorbent material. Such superabsorbent material is well known in the field of absorbent articles and is constituted by water-swellable and water-insoluble material which is capable of absorbing large quantities of fluid upon formation of a hydrogel. The absorbent core 161 may contain superabsorbent material in the form of fibers or particles of absorbent polymer material. For example, the superabsorbent material may be surface cross-linked, partially neutralized polyacrylates. The superabsorbent material e.g., the superabsorbent fibers or particles, may be mixed with other absorbent or liquid uptake material or materials, such as cellulose fluff pulp, and/or be arranged in pockets or layers in the absorbent core 161.

The absorbent core 161 may further comprise components for improving properties of the absorbent core 161, such as integrity and strength. For example, the absorbent core 161 may comprise a binder or binders, such as binder fibers. Resilient fibers, chemically stiffened fibers, etc. may be present in the absorbent core 161 to counteract wet-collapse of cellulosic fibers. Such fibers may also be useful in retaining a fluid transporting capillary network in the absorbent component so that absorbent fluid may be distributed in the absorbent component and be absorbed by superabsorbent material also in parts of the absorbent component outside the initial wetting area of the absorbent article.

The topsheet 163 is a wearer-facing layer and may comprise or consist of a fluid permeable nonwoven fabric, a perforated polymer film, mesh or foam. The topsheet may be made from thermoplastic material, such as thermoplastic synthetic fibers, film or netting. The topsheet 163 may consist of a single layer or may have a laminate structure comprising a plurality of layers, for example, two or more layers. The layers may be made of the same material, or some or all layers may be made of different materials.

Furthermore, the backsheet 162 may be constituted by a liquid-impermeable layer such as a polymeric film, for example a film of polyethylene or polypropylene. The backsheet 162 may be breathable. The materials which may be used for the backsheet 162 include thin and flexible fluid impermeable plastic films, or fluid impermeable nonwoven materials, fluid impermeable foams and fluid impermeable laminates. The backsheet 162 may be formed by a single layer, or may be a multi-layered structure, with at least one layer being fluid impermeable.

After the application and attachment of an absorbent assembly 160 to the composite web 130 of interconnected precursor articles 131*a*, 131*b*, 131*c*, leg cuts 170 are formed in the composite web 130 of interconnected precursor articles 131*a*, 131*b*, 131*c* between the precursor articles 131*a*, 131*b*, 131*c*, each leg cut 170 having a closed loop configuration as indicated between the precursor articles 131*b* and 131*c* in FIG. 7. The leg cuts form a first leg edge 171 of the leading precursor article 131*c* and a second leg edge 172 of the trailing precursor article 131*b*;

As shown in FIG. 7, the closed-loop leg cuts 170 form cut-out portions 173 having an approximate heart-shape inside each leg cut 170. The shape of the leg cuts 170 and the outline of the cut-out portions is not limiting to the method or the pant-type absorbent article as disclosed herein and may be varied within the scope of the appended claims. By way of example, the leg edges of the pant-type absorbent article 1 which is shown in FIGS. 1-3 has a slightly different leg outline but can still be produced with a method as described in connection with FIGS. 4-9.

After forming the leg cuts 170, the cut-out portions 173 are removed from the composite web 130 of interconnected precursor articles 131*a*, 131*b*, 131*c* and are not further part of the process as disclosed herein.

After forming the leg cuts, the absorbent assemblies 160 will be located centrally between the first leg edge 171 and the second leg edge 172 of each precursor article 131*a*, 131*b*, 131*c* in the composite web 130 of interconnected precursor articles 131*a*, 131*b*, 131*c*.

Figure 9:
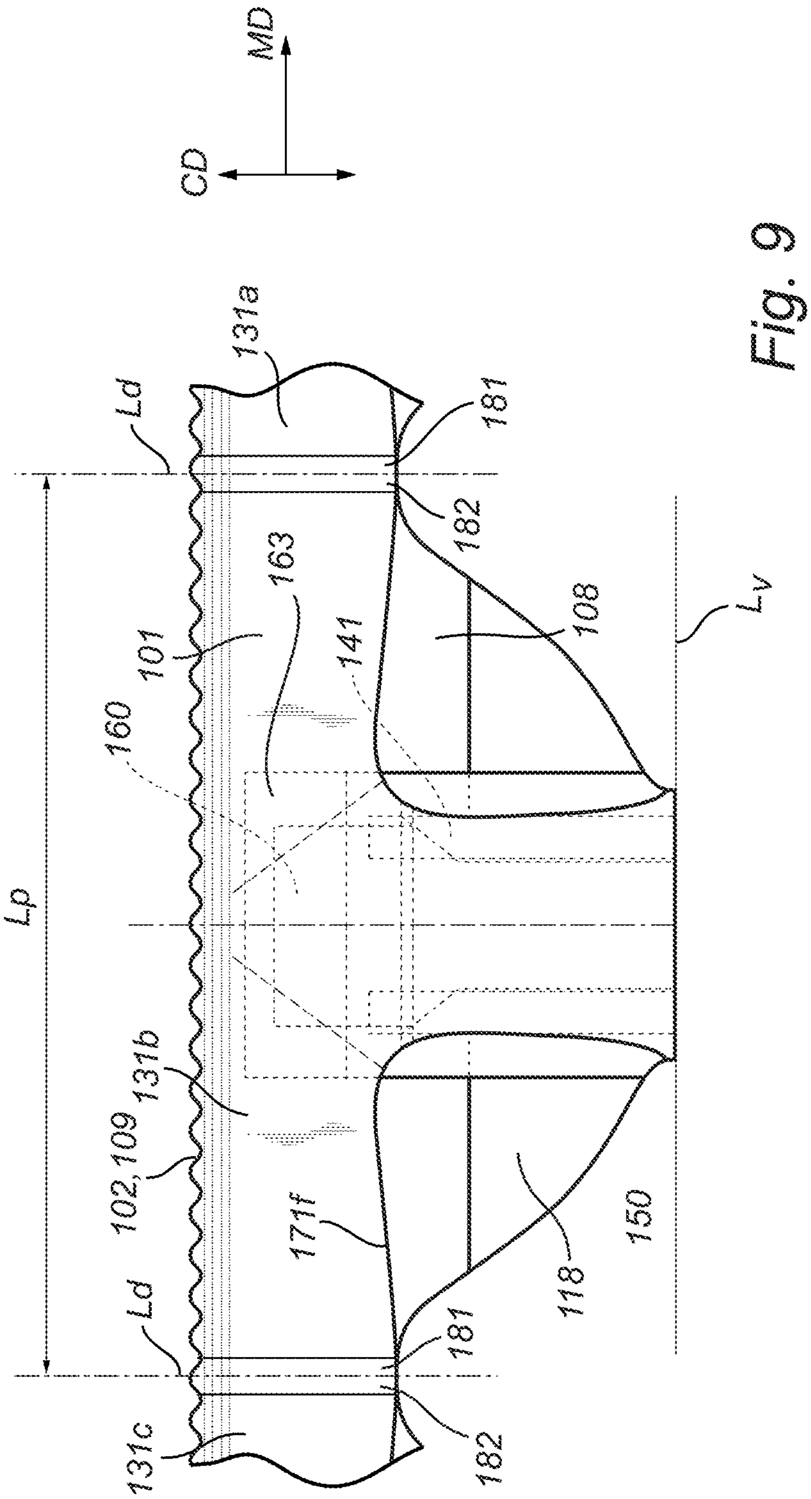

As is shown in FIG. 9, when the leg edges 171, 172 have been formed, the composite web 130 of interconnected precursor articles 131*a*, 131*b*, 131*c* is folded along a fold-line Lv extending in the machine direction MD to bring the waist edge 102 of the front panel web 101 into alignment with the waist edge 109 of the rear panel web 108.

A first side seam 181 and a second side seam 182 are formed in each precursor article 131*a*, 131*b*, 131*c* along the dividing lines Ld between the precursor articles 131*a*, 131*b*, 131*c*, from the aligned waist edges 102, 109 of the front and rear panel webs 101, 108, to the leg cuts 170.

The first side seam 181 of a leading precursor article 131*a* and the second side seam 182 of a trailing precursor article 131*b* may be formed as a single broad seal extending along the dividing line Ld, as shown in FIG. 9. When cutting away individual pant-type articles from the chassis web 130 of precursor articles 131*a*, 131*b*, 131*c* by severing the composite web 130 of interconnected precursor articles 131*a*, 131*b*, 131*c* along the dividing lines Ld, the single broad seal shown in FIG. 9 will at the same time be divided into the two side seams 181, 182 of the interconnected precursor articles 131*a*, 131*b*.

Alternatively, the side seams 181, 182 may be formed as individual seals placed on each side of the dividing line Ld.

The side seams may be formed by any method suitable for the purpose, such as by thermo-welding, ultrasonic welding or by means of adhesive. In case of adhesive side seals, the adhesive is generally applied before the chassis web is folded along the folding line Lv.

The method as disclosed herein may further comprise attaching reinforcing leg elastic along all or selected parts of the leg openings.

Figure 10:
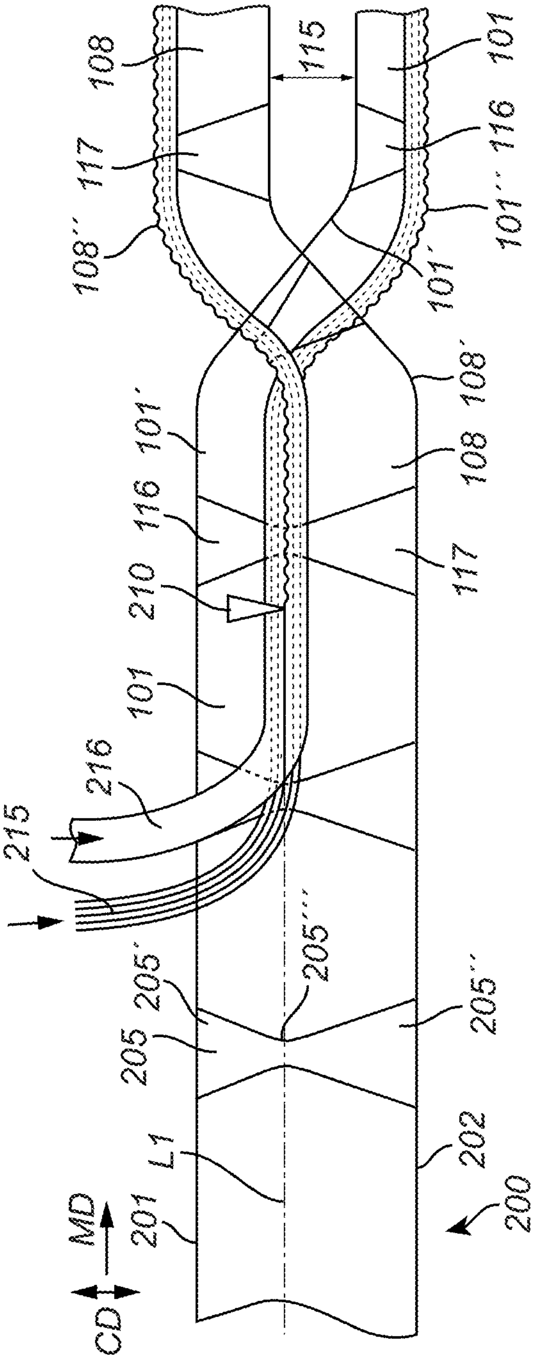
FIG. 10 shows a planar view of a method for producing body panel webs.
Figure 11:
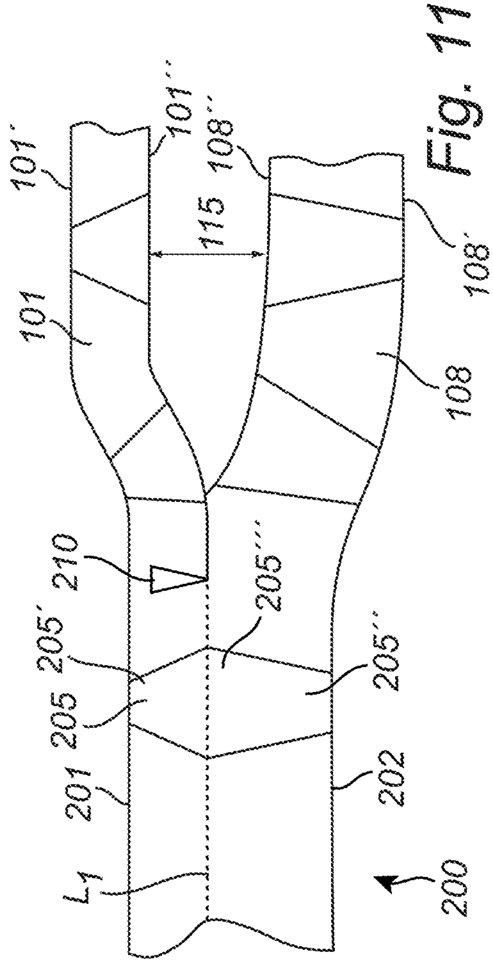
FIG. 11 shows a planar view of a further method for producing body panel webs.

As shown in FIGS. 10 and 11, the zones of reduced elasticity 116, 117 may be formed in an elastic material web 200 which is a precursor web for forming a first and a second body panel web 101,108, such as a front and a rear body panel web 101,108. The elastic material web 200 is divided into the front and the rear body panel web 101, 108 after formation of the zones of reduced elasticity 116,117.

The method steps which are shown in FIGS. 10 and 11 are performed prior to arranging a tensioned front body panel web 101 and a tensioned rear body panel web 108 side-by side as shown in FIG. 4.

The tensioned first body panel web 101 and the tensioned second body panel web 108 are formed from a single elastic web material 200 having a first side edge 201 and a second side edge 202 and which is heat-treated to form zones 205 of reduced elasticity. The tensioned elastic web material 200 is subsequently divided in two parts by forming a cut 210 in the elastic web material 200 along a dividing line L1 extending in the machine direction MD, as shown in FIGS. 10 and 11, thereby forming the tensioned first body panel web 101 and the tensioned second body panel web 108 from the heat-treated elastic web material 200. The tensioned first body panel web 101 has a first side edge 101' being constituted by the first side edge 201 of the elastic web material 200 and having a second side edge 101" being formed by the cut 210 in the elastic web material, the tensioned second body panel web 108 having a first side edge 108' being constituted by the second side edge 202 of the elastic web material 200 and a second side edge 108" being formed by the cut 210 in the elastic web material 200.

As shown in FIG. 10, the step in the method as disclosed herein of arranging the tensioned first body panel web 101 and the tensioned second body panel web 108 side-by-side at a distance 115 from each other in the cross machine direction, CD, may involve shifting position of the first body panel web 101 and the second body panel web 108 which are formed by dividing a tensioned elastic web material 200. Thereby, the second side edge 101" of the tensioned first body panel web forms the first waist edge 102 of a composite web of precursor articles 130 as shown in FIGS. 4-8 and the second side edge of 108" of the tensioned second body panel web 108 forms the second waist edge 109 of a composite web of precursor articles 130 as shown in FIGS. 4-8.

With reference to FIG. 10, waist elastic 215 is applied to the elastic web material 200 along the dividing line L1 in the elastic web material 200, before forming the cut 210 in the elastic web material 200. The cut 210 is subsequently formed through the elastic web material 200 and through the waist elastic 215 which is applied and attached to the elastic web material 200. In the example in FIG. 10, the waist elastic 215 is applied in the form of multiple elastic elements which are subsequently covered by a nonwoven covering web 216. It is to be understood that the waist elastic may be applied in any useful form, such as in the form of a pre-fabricated band-shaped waist elastic member which may comprise one or more elastic elements such as bands, strings, elastic film, elastic nonwoven, etc.

As is shown in FIGS. 10 and 11, the zones with reduced elasticity 205 which are formed in the elastic web material 200 are each divided in a first part 116 and a second part 117 by the cut 210 in the elastic web material 210 with the first part 116 of each zone with reduced elasticity 205 of the original elastic web material 200 being located in the tensioned first body panel web 101 and the second part 117 of each zone with reduced elasticity 205 being located in the tensioned second body panel web 108.

In FIG. 10, the zones with reduced elasticity 205 which are formed in the elastic web material 200 have a shape with a first end portion 205' and a second end portion 205" and an intermediate portion 205'" between the first end portion 205' and the second end portion 205", as seen in the cross machine direction CD. The first end portion 205' and the second end portion 205" have a greater width in the machine direction MD than a width in the machine direction MD of the intermediate portion 205'". The cut 210 in the elastic web material 200 divides each zone with reduced elasticity 205 in the narrow intermediate portion 205'" of the zone with reduced elasticity 205.

FIG. 11 shows an alternative way of performing the step of arranging the tensioned first body panel web 101 and the tensioned second body panel web 108 side-by-side at a distance 115 from each other in the cross machine direction, CD, wherein the first body panel web 101 and the second body panel web 108 which are formed by dividing a tensioned elastic web material 200 are pulled apart in the cross machine direction CD, whereby the first side edge 101' of the tensioned first body panel web 101 forms the first waist edge 102 of the composite web of precursor articles 130 as shown in FIGS. 4-8 and the first side edge 108' of the tensioned second body panel web 108 forms the second waist edge 109 of the composite web of precursor articles 130 as shown in FIGS. 4-8.

In the method shown in FIG. 11, waist elastic may be applied along the first and second side edges 201,202 of the elastic web material 200 before or after forming the cut 210 in the elastic web material 200.

In both the method shown in FIG. 10 and the method shown in FIG. 11, waist elastic may be omitted. It is also to be understood that waist elastic may be added at the waist edges of a composite web of precursor articles at any stage of the process up until severing of individual absorbent pant-type articles from the composite web of precursor articles.

As shown in FIG. 11, the zones with reduced elasticity 205 which are formed in the elastic web material 200 may have a shape with a first end portion 205' and a second end portion 205" and an intermediate portion 205'" between the first end portion 205' and the second end portion 205", as seen in the cross machine direction CD. The first end portion 205' and the second end portion 205" have a smaller width in the machine direction MD than a width in the machine direction MD of the intermediate portion 205;40 ". The cut 210 in the elastic web material 200 divides each zone with reduced elasticity 205 in the wider intermediate portion 205'" of the zone with reduced elasticity 205.

A further option of providing a tensioned first body panel web 101 and a tensioned second body panel web 108, is to supply the body panel webs 101, 108 as separate elastic material webs 200. Such option offers the advantage that the first body panel web 101 and the second body panel web may be freely selected from different materials, e.g., from materials with different elastic properties.

Figure 12:
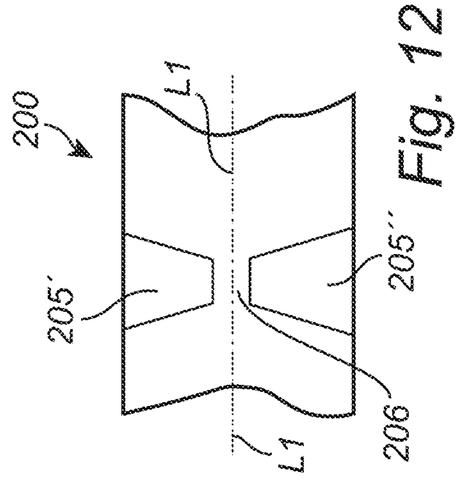
FIG. 12 shows an alternative way of forming zones of reduced elasticity in the method in FIG. 10.

FIG. 12 shows a further alternative for forming heat treated zones of reduced elasticity 205',205" in a tensioned elastic web material 200. The difference from the method shown in FIG. 10 is that the part of the tensioned elastic web material 200 which is to form the first tensioned body panel web 101 is provided with a first part zone of reduced elasticity 205' and the part of the tensioned elastic web material 200 which is to form the second tensioned body panel web 108 is provided with a second part zone of reduced elasticity 205", the first and second zones of reduced elasticity 205', 205" forming the first and second zones of reduced elasticity 116, 117 in the first and second tensioned body panel webs 101, 108. The first and second part zones of reduced elasticity 205',205" are arranged spaced apart in the cross machine direction CD, leaving an area 206 at the dividing line L1 which is not subjected to heat treatment and which retains its original elastic properties. The spacing between the first and second part zones of reduced elasticity 205',205" is preferably sufficient to allow application of waist elastic in the non-treated part of the elastic web material.

Description Of Test Methods

Elasticity test

The method is used to determine if a material can be considered elastic, by determining the extent of permanent deformation after two loading and unloading cycles.

A suitable tensile tester, such as available from e.g., the Lloyd, Instron or Zwick companies, is used. The tensile tester should be equipped with two vertically aligned clamps and be able to perform cyclic movements.

The tested material should be conditioned for at least 4 hours in an environment set to 23° C. ±2° C. and 50% ±5% relative humidity. Testing takes place in this same environment.

For a stable subsequent attachment into the tensile tester clamps, high friction tape may be attached over the front and back sides of the sample strips, just outside of a tested 50 mm middle section of the sample.

Sample strips, 25 mm wide and preferably at least 100 mm long, are cut from the tested material using a scalpel and a cutting template.

The clamps of the tester should be as wide or wider than the tested sample. At the start of the procedure, the clamps are set at a mutual distance of 50 mm, equaling the tested length of the sample.

The method may be used for determining the cross machine direction elasticity or the machine direction elasticity of a material depending on which direction is aligned with the length direction of the sample. Accordingly, the method measures the elasticity in the length direction of the sample.

When testing parts of an article as disclosed herein, the functionality of the tested portion of the article should be considered when preparing the sample strips. For example, elasticity of a panel material in a pant diaper is generally evaluated with the length direction of the sample arranged parallel to the waist edge, in the transverse direction of the article, as this is the main direction of stretch when the article is in use. However, it is also possible to evaluate the elasticity of the article in the length direction with the method described herein.

The tensile tester is calibrated according to the apparatus instructions.

The load and clamp distance on the tensile tester are zeroed. The sample is inserted (vertically centered) into the clamps and a very slight stress (preload) of 0.05 N±0.01 N is applied over the sample. This is the starting point for the test. The upper clamp is set to move at a speed of 500 mm/min for a 15 mm distance, equaling a 30% extension from the initial 50 mm sample length, and then to immediately return to the starting point at the same speed.

A first cycle of elongation and return to the starting point is performed and is immediately followed by an identical second cycle. A pre-test value for elongation of the sample is recorded at 0.1 N at the beginning of the first cycle. After performing the second cycle, the sample is allowed to rest for 60 seconds while remaining fastened in the clamps at the starting point. Thereafter, the sample is stretched until a force of 0.1 N is registered and the post-test elongation of the sample is recorded as the elongation of the sample at 0.1 N. The permanent deformation of the sample is calculated by dividing the difference (δ) between the post-test elongation and the pre-test elongation at 0.1 N with the pre-test elongation at 0.1 N.

For example, at the post-test stretch to 0.1 N, an elongation of 5 mm is read. The elongation (5 mm) is then divided by the initial length of the sample (50 mm), giving a permanent deformation of 10%.

In the context of this disclosure, a material is considered to be elastic if the permanent deformation is less than 10% and is considered to be non-elastic if the permanent deformation exceeds 10%.

Comparison of Elasticity in Different Zones of a Material

The test method for panel zone elasticity follows the general set up of standard method ASTM D882-18, with some adaptions and modifications as specified in the instructions below.

All preparations and testing take place in a laboratory environment set to 23° C. +/−1° C. and 50% +/−5% relative humidity.

The tests are carried out on samples taken from elastic body panels having a crotch edge and a waist edge and being formed from elastic web material which has been heat treated to form zones with reduced elasticity in the body panels. The tests are carried out on the elastic web material of the elastic body panels, i.e., without any additional elastic or non-elastic components.

Test samples are taken from the heat-treated body panels. The samples are 25 mm wide and at least 100 mm long. All samples are cut with the length direction of the sample parallel with the transverse direction of the panels, i.e., parallel to the crotch and waist edges of the panels. For this purpose, a metal template is placed on top of a panel, and a sample is prepared by cutting with a scalpel along the template periphery. A first set of 10 samples is centered such that a 50 mm long mid-section of the sample is entirely within the zone of reduced elasticity. A second set of samples is centered such that the 50 mm long mid-section is entirely outside of the zone with reduced elasticity.

For a stable subsequent attachment into the tensile tester clamps, high friction tape may be attached over the front and back sides of the sample strips, just outside of the tested 50 mm middle section of the sample.

The elasticity test should be finalized within 10 minutes from cutting the sample from the panel to minimize creep in the elastic material.

A conventional tensile tester is used for the test (available e.g., from the Zwick/Roell, Instron or Lloyd companies). The upper and lower clamps should be at least 25 mm wide, and vertically aligned. The gauge length (test length) between the clamps is set to 50 mm. The force reading of the tensile tester is zeroed, and the taped sections of the sample are inserted into the clamps. After insertion, the sample pre-tension should be 0.05N +/−0.01 N (as indicated on the force display). The upper clamp is then set to move at a constant speed of 500 mm/min. When the tensile tester reads a force of 5 N, percentual extension of the sample is calculated.

For example, the test length of 50 mm is inserted into the clamps. The upper clamp moves, and 5 N is read after 70 mm (or a total 120 mm clamp separation). The reported elasticity at 5 N equals the 70 mm extension divided by the initial 50 mm sample length, or 140%.

An elasticity value in the context of this disclosure is the arithmetic mean from a series of 10 representative individual samples.

The invention claimed is:

1. A disposable pant-type article, the article having a longitudinal direction and a transverse direction, the article comprising:

a front body panel being constituted by an elastic front body panel material, the front body panel material being elastically stretchable in the transverse direction;

a rear body panel being constituted by an elastic rear body panel material, the rear body panel material being elastically stretchable in the transverse direction;

a crotch region being located between the front body panel and the rear body panel;

an absorbent core being arranged with a central part of the absorbent core being located in the crotch region(s) and with a front end part of the absorbent core overlapping with the front body panel in a front overlap area and with a rear end part of the absorbent core overlapping with the rear body panel in a rear overlap area;

a first front panel side edge being joined to a first rear panel side edge in a first side seam;

a second front panel side edge being joined to a second rear panel side edge in a second side seam;

a waist opening, defined by a front panel waist edge and a rear panel waist edge;

a first leg edge defining a first leg opening; and a second leg edge defining a second leg opening;

the disposable pant-type article further comprising at least one body panel zone with reduced elasticity, the at least one body panel zone with reduced elasticity being arranged in the overlap area between the absorbent core and one of the front body panel and the rear body panel, the at least one body panel zone with reduced elasticity extending in the longitudinal direction outside the overlap area towards the waist opening, and having a tapering shape in the longitudinal direction of the disposable pant-type article, with an extension of the at least one body panel zone with reduced elasticity in the transverse direction adjacent the waist opening being smaller than an extension of the at least one body panel zone with reduced elasticity in the transverse direction (adjacent the absorbent core.

2. A disposable pant-type article according to-any claim 1, wherein the absorbent core forms part of an absorbent assembly, the absorbent assembly comprising the absorbent core, a liquid permeable topsheet and a liquid impermeable backsheet, the absorbent core being sandwiched between the liquid permeable topsheet and the liquid impermeable backsheet.

3. A disposable pant-type article according to claim 1, wherein the at least one body panel zone with reduced elasticity is a front body panel zone with reduced elasticity, the at least one body panel zone with reduced elasticity being arranged in the overlap area between the absorbent core and the front body panel.

4. A disposable pant-type article according to claim 3, wherein the disposable pant-type article further comprises a rear body panel zone with reduced elasticity, the rear body panel zone with reduced elasticity being arranged in the overlap area between the absorbent core and the rear body panel, the rear body panel zone with reduced elasticity extending in the longitudinal direction outside the overlap area towards the waist opening, and having a tapering shape in the longitudinal direction of the disposable pant-type article, with an extension of the rear body panel zone with reduced elasticity in the transverse direction adjacent the waist opening being smaller than an extension of the rear body panel zone with reduced elasticity in the transverse direction adjacent the absorbent core.

5. A disposable pant-type article according to claim 4, wherein the elasticity of the body panel material in the front body panel zone with reduced elasticity or wherein the elasticity of the body panel material in the rear body panel zone with reduced elasticity is from 0% to 70% of the elasticity of the body panel material outside the body panel zone with reduced elasticity.

6. A disposable pant-type article according to claim 3, wherein a tapering angle is defined between a line of inclination of a portion of the front body panel zone with reduced elasticity which is located between a forward end edge of the absorbent assembly and a front waist edge of the front body panel, and a line, which is parallel to the longitudinal direction of the pant-type absorbent article.

7. A disposable pant-type article according to claim 6, wherein the tapering angle (α) of the front body panel zone with reduced elasticity is in the range of from 3° to 35°.

8. A disposable pant-type article according to claim 4, wherein a tapering angle is defined between a line of inclination of a portion of the rear body panel zone with reduced elasticity which is located between a rearward end edge of the absorbent assembly and a rear waist edge of the rear body panel, and a line, which is parallel to the longitudinal direction of the pant-type absorbent article;

or the tapering angle of the rear body panel zone with reduced elasticity.

9. A disposable pant-type article according to claim 8, wherein the tapering angle of the rear body panel zone with reduced elasticity is in the range of from 3° to 35°.

10. A disposable pant-type article according to claim 1, wherein the at least one body panel zone with reduced elasticity has a continuously tapering shape in a part of the body panel zone with reduced elasticity which is arranged between an end edge of the absorbent core and the waist edge of the body panel in which the body panel zone with reduced elasticity is arranged or wherein the at least one body panel zone with reduced elasticity has a continuously tapering shape in a part of the body panel zone with reduced elasticity which is arranged between an end edge of the absorbent assembly and the waist edge of the body pane in which the body panel zone with reduced elasticity is arranged.

11. A disposable pant-type article according to-any claim 1, wherein the at least one body panel zone with reduced elasticity has a triangular shape, a trapezoidal shape or a funnel shape.

12. A disposable pant-type article according to claim 1, wherein the elastically stretchable front body panel material or the elastically stretchable rear body panel material comprises of an elastic laminate, the elastic laminate comprising at least a first layer of nonwoven material and an elastic layer.

13. A disposable pant-type article according to claim 12, wherein the first layer of nonwoven material is a non-elastic layer.

14. A disposable pant-type article according to claim 12, wherein the elastic laminate comprises a second layer of nonwoven material and the elastic layer is an intermediate elastic layer arranged between the first and second layers of nonwoven material.

15. A disposable pant-type article according to claim 14, wherein the second layer of nonwoven material is a non-elastic layer.

16. A disposable pant-type article according to claim 12, wherein the elastic layer comprises or consists of a layer of elastic film.

17. A disposable pant-type article according to claim 12, wherein the elastic layer comprises a layer of elastic non-woven material.

18. A disposable pant-type article according to claim 12, wherein at least two layers of the elastic laminate are bonded together with a plurality of discrete bonds, the bonds being arranged in a regular bonding pattern, the bonding pattern being visible on an external surface of the elastic body panel including being visible on the external surface of the elastic body panel in the body panel zone.

19. A disposable pant-type article according to claim 1, wherein the elastically stretchable front body panel or the elastically stretchable rear body panel comprises or consists of an elastic nonwoven material.

20. A disposable pant-type article according to claim 1, wherein the elastically stretchable front body panel is formed from a continuous front body panel web which extends transversely across the width of the pant-type article between the first and the second front panel side edges or wherein the elastically stretchable rear body panel is formed from a continuous rear body panel web which extends transversely across the width of the pant-type article between the first and the second rear panel side edges.

21. A disposable pant-type article according to claim 1, wherein the crotch region comprises a non-elastic crotch web material.

22. A disposable pant-type article according to claim 1, wherein the disposable pant-type article comprises an elastic waist feature , the elastic waist feature comprising one or more elastic elements.

23. A disposable pant-type article according to claim 22, wherein the elastic waist feature is completely overlapping with the front body panel and with the rear body panel and shares a waist edge with the corresponding front body panel and rear body panel.

24. A disposable pant-type article according to claim 22, wherein the elastic waist feature is applied to a waist edge of the front body panel and the rear body panel and protrudes beyond the waist edge of the corresponding front body panel or rear body panel.

25. A disposable pant-type article according to claim 22, wherein the elastic waist feature extends around the full circumference of the waist opening in the form of a waistband.

26. A disposable pant-type article according to claim 22, wherein the elastic waist feature is a component of the disposable pant-type article which is distinct from the body panel material of the front body panel and the rear body panel.

27. A method of producing a disposable pant-type article, the method comprising:

continuously feeding a tensioned elastic web material in a machine direction, the elastic web material having a first side edge and a second side edge;

creating zones with reduced elasticity in the elastic web material by exposing portions of the elastic web material to heat treatment, the zones with reduced elasticity being spaced-apart in the machine direction;

forming at least a first body panel web as a part of a composite web of interconnected precursor articles from the elastic web material, the composite web of precursor articles having a first waist edge and a second waist edge, the tensioned first body panel web comprising at least a portion of each of the spaced-apart zones with reduced elasticity each portion of each of the spaced-apart zones with reduced elasticity forming a body panel zone with reduced elasticity in the first body panel web, each body panel zone with reduced elasticity having a tapering shape in the cross machine direction of the tensioned first body panel web;

arranging the tensioned first body panel web side-by-side with a tensioned elastic second body panel web in the composite web of interconnected precursor articles and with a distance between the tensioned first body panel web and the tensioned second body panel web in a cross machine direction and with the body panel zones with reduced elasticity in the first body panel web arranged with each body panel zone with reduced elasticity tapering towards the first waist edge of the composite web of precursor articles;

intermittently applying absorbent assemblies to the tensioned first body panel web and the tensioned second body panel web, the absorbent assemblies being applied spaced-apart in the machine direction and being attached with a first end part of each absorbent assembly overlapping a zone of reduced elasticity in the tensioned first body panel web and a second end part of the absorbent assembly; overlapping a portion of the tensioned second body panel web;

folding the composite web of precursor articles along a fold-line extending in the machine direction and bringing the first waist edge of the composite web of precursor articles into alignment with the second waist edge of the composite web of precursor articles;

forming first and second side seams in each precursor article, the side seams joining the tensioned first body panel web with the tensioned second body panel web and being formed in the cross machine direction along dividing lines between the precursor articles; and severing individual pant-type articles from the composite web of precursor articles.

28. A method according to claim 27, wherein the method further comprises:

feeding a continuous non-elastic crotch web in the machine direction;

attaching the non-elastic crotch web to the tensioned first body panel web and to the tensioned second body panel web, thereby bridging the distance between the tensioned first body panel web and the tensioned second body panel web, the non-elastic continuous crotch web being attached to the tensioned first body panel web and to the tensioned second body panel web after arranging the tensioned first body panel web side-by-side with the tensioned elastic second body panel web and before applying the absorbent assemblies to the tensioned first body panel web and to the tensioned second body panel web; and forming leg cuts in the composite web of interconnected precursor articles, each leg cut having a closed loop configuration and forming a first leg edge of a leading precursor article and a second leg edge of a trailing precursor article.

29. A method according to claim 28, wherein the method further comprises:

providing a pair of crotch elastic members, the pair of crotch elastic members consisting of a first crotch elastic member and a second crotch elastic member;

stretching each crotch elastic member in a longitudinal direction of the crotch elastic member and aligning the longitudinal direction of the crotch elastic member with the cross machine direction;

attaching each stretched crotch elastic member to the crotch web while keeping the crotch elastic member stretched and aligned with the cross machine direction, the first crotch elastic member being spaced apart from the second crotch elastic member with a crotch spacing in the machine direction, a pair of crotch elastic members of a leading precursor article being spaced apart from a pair of crotch elastic members of a trailing precursor article with an article spacing in the machine direction, the article spacing being dependent on a pitch-length of the precursor articles in the composite web of interconnected precursor articles.

30. A method according to claim 27, wherein the method further comprises:

dividing the tensioned heat-treated elastic web material in two parts by forming a cut in the elastic web material along a dividing line extending in the machine direction, thereby forming the tensioned first body panel web and the tensioned second body panel web from the heat-treated elastic web material, the tensioned first body panel web having a first side edge being constituted by the first side edge of the elastic web material and having a second side edge being formed by the cut in the elastic web material, the tensioned second body panel web having a first side edge being constituted by the second side edge of the elastic web material and a second side edge being formed by the cut in the elastic web material.

31. A method according to claim 30, wherein the step of arranging the tensioned first body panel web and the tensioned second body panel web side-by-side at a distance from each other in the cross machine direction involves shifting position of the tensioned first body panel web and the tensioned second body panel web in the cross machine direction, whereby the second side edge of the tensioned first body panel web forms the first waist edge of the composite web of precursor articles and the second side edge of the tensioned second body panel web forms the second waist edge of the composite web of precursor articles.

* * * * *